United States Patent
Shelton, IV et al.

(10) Patent No.: US 12,213,668 B2
(45) Date of Patent: Feb. 4, 2025

(54) FIRING SYSTEM FEATURES FOR SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Adam D. Hensel, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 602 days.

(21) Appl. No.: 17/402,695

(22) Filed: Aug. 16, 2021

(65) Prior Publication Data
US 2023/0050707 A1    Feb. 16, 2023

(51) Int. Cl.
*A61B 17/072*    (2006.01)
*A61B 17/00*    (2006.01)

(52) U.S. Cl.
CPC .. *A61B 17/072* (2013.01); *A61B 2017/00367* (2013.01); *A61B 2017/0725* (2013.01); *A61B 2017/07271* (2013.01)

(58) Field of Classification Search
CPC ........ A61B 17/072; A61B 2017/00367; A61B 2017/0725; A61B 2017/07271;
(Continued)

(56) References Cited

U.S. PATENT DOCUMENTS

| | | | | |
|---|---|---|---|---|
| 4,473,077 A | * | 9/1984 | Noiles | A61B 17/115 227/19 |
| 4,527,724 A | * | 7/1985 | Chow | A61B 17/072 227/19 |

(Continued)

FOREIGN PATENT DOCUMENTS

| | | |
|---|---|---|
| EP | 3000410 A2 | 3/2016 |
| EP | 3420936 A1 | 1/2019 |

(Continued)

OTHER PUBLICATIONS

U.S. Appl. No. 17/402,674, entitled "Surgical Stapler End Effector Sled Having Cartridge Wall Support Feature," filed Nov. 4, 2020.

(Continued)

*Primary Examiner* — Robert F Long
(74) *Attorney, Agent, or Firm* — Frost Brown Todd LLP

(57) ABSTRACT

A surgical stapling instrument includes a shaft assembly and an end effector. The end effector includes a first jaw having an anvil, and a second jaw. The instrument also includes a stapling assembly supported by the second jaw and including a plurality of staples, a staple actuator, and a driver assembly. The driver assembly includes a laterally-opposed pair of distal drivers that receive respective staples, a proximal driver that receives a respective staple, and a cam surface. The staple actuator is configured to engage the cam surface during distal translation of the staple actuator to drive the respective staples into contact with the anvil. The staple actuator and the cam surface are configured such that, when the respective staples contact the anvil, the engagement between the staple actuator and the cam surface is centered at a location along the cam surface distal of a centroid of the first driver assembly.

20 Claims, 22 Drawing Sheets

(58) Field of Classification Search
CPC ........... A61B 2017/07228; A61B 2017/07278; A61B 2090/036; A61B 17/07207
USPC ................................ 227/175.1–182.1, 8, 19
See application file for complete search history.

(56) References Cited

U.S. PATENT DOCUMENTS

| | | | | |
|---|---|---|---|---|
| 4,978,049 | A * | 12/1990 | Green | A61B 17/07207 227/21 |
| 5,129,570 | A | 7/1992 | Schulze et al. | |
| 5,364,003 | A * | 11/1994 | Williamson, IV | A61B 17/0644 227/19 |
| 5,415,334 | A * | 5/1995 | Williamson, IV | A61B 17/07207 227/19 |
| 5,485,952 | A * | 1/1996 | Fontayne | A61B 17/07207 227/111 |
| 5,630,540 | A * | 5/1997 | Blewett | A61B 17/07207 227/176.1 |
| 6,786,382 | B1 * | 9/2004 | Hoffman | A61B 17/07207 227/180.1 |
| 7,404,508 | B2 | 7/2008 | Smith et al. | |
| 7,434,715 | B2 | 10/2008 | Shelton, IV et al. | |
| 7,721,930 | B2 | 5/2010 | McKenna et al. | |
| 7,810,692 | B2 | 10/2010 | Hall et al. | |
| 7,832,408 | B2 | 11/2010 | Shelton, IV et al. | |
| 7,845,537 | B2 | 12/2010 | Shelton, IV et al. | |
| 8,083,120 | B2 | 12/2011 | Shelton, IV et al. | |
| 8,210,411 | B2 | 7/2012 | Yates et al. | |
| 8,408,439 | B2 | 4/2013 | Huang et al. | |
| 8,453,914 | B2 | 6/2013 | Laurent et al. | |
| 8,708,213 | B2 | 4/2014 | Shelton, IV et al. | |
| 9,060,770 | B2 | 6/2015 | Shelton, IV et al. | |
| 9,186,142 | B2 | 11/2015 | Fanelli et al. | |
| 9,517,065 | B2 | 12/2016 | Simms et al. | |
| 9,622,746 | B2 | 4/2017 | Simms et al. | |
| 9,717,497 | B2 | 8/2017 | Zerkle et al. | |
| 9,795,379 | B2 | 10/2017 | Leimbach et al. | |
| 9,808,248 | B2 | 11/2017 | Hoffman | |
| 9,839,487 | B2 | 12/2017 | Dachs, II | |
| 10,011,018 | B2 | 7/2018 | McGrogan et al. | |
| 10,092,292 | B2 | 10/2018 | Boudreaux et al. | |
| 10,307,170 | B2 | 6/2019 | Parfett et al. | |
| 10,335,147 | B2 * | 7/2019 | Rector | A61B 17/068 |
| 10,390,823 | B2 * | 8/2019 | Shelton, IV | A61B 17/072 |
| 10,485,621 | B2 | 11/2019 | Morrissette et al. | |
| 10,537,400 | B2 | 1/2020 | Dachs, II et al. | |
| 10,610,313 | B2 | 4/2020 | Bailey et al. | |
| 10,639,033 | B2 * | 5/2020 | Beardsley | A61B 17/0644 |
| 10,667,809 | B2 | 6/2020 | Bakos et al. | |
| 10,806,530 | B2 | 10/2020 | Liao et al. | |
| 10,863,988 | B2 | 12/2020 | Patel et al. | |
| 11,020,109 | B2 * | 6/2021 | Baxter, III | A61B 17/064 |
| 11,020,138 | B2 | 6/2021 | Ragosta | |
| 11,026,755 | B2 | 6/2021 | Weir et al. | |
| 11,076,926 | B2 | 8/2021 | Ragosta et al. | |
| 11,147,552 | B2 | 10/2021 | Burbank et al. | |
| 11,166,773 | B2 | 11/2021 | Ragosta et al. | |
| 11,234,700 | B2 | 2/2022 | Ragosta et al. | |
| 11,259,884 | B2 | 3/2022 | Burbank | |
| 11,382,624 | B2 * | 7/2022 | Harris | A61B 17/068 |
| 11,690,619 | B2 * | 7/2023 | Shelton, IV | A61B 17/105 227/178.1 |
| 2001/0031975 | A1 * | 10/2001 | Whitman | A61B 34/71 606/167 |
| 2003/0050628 | A1 * | 3/2003 | Whitman | A61B 17/00234 606/1 |
| 2006/0074407 | A1 * | 4/2006 | Padget | A61B 17/3201 606/1 |
| 2006/0185682 | A1 | 8/2006 | Marczyk | |
| 2006/0278680 | A1 * | 12/2006 | Viola | A61B 17/068 227/176.1 |
| 2007/0175956 | A1 * | 8/2007 | Swayze | A61B 34/76 227/19 |
| 2007/0194081 | A1 * | 8/2007 | Hueil | B25C 5/0292 227/176.1 |
| 2008/0023522 | A1 | 1/2008 | Olson et al. | |
| 2008/0245841 | A1 * | 10/2008 | Smith | A61B 17/115 227/175.2 |
| 2010/0076461 | A1 * | 3/2010 | Viola | A61B 17/0469 606/144 |
| 2010/0213240 | A1 * | 8/2010 | Kostrzewski | A61B 17/3209 227/180.1 |
| 2010/0280605 | A1 * | 11/2010 | Hammer | A61B 17/068 623/2.11 |
| 2011/0147433 | A1 * | 6/2011 | Shelton, IV | A61B 34/30 227/176.1 |
| 2011/0290853 | A1 * | 12/2011 | Shelton, IV | A61B 17/0682 227/177.1 |
| 2012/0209314 | A1 | 8/2012 | Weir et al. | |
| 2013/0092719 | A1 * | 4/2013 | Kostrzewski | A61B 17/105 227/177.1 |
| 2013/0119109 | A1 * | 5/2013 | Farascioni | A61B 17/07207 227/175.1 |
| 2014/0166725 | A1 * | 6/2014 | Schellin | B29C 43/00 227/178.1 |
| 2014/0183244 | A1 * | 7/2014 | Duque | A61B 17/068 606/167 |
| 2014/0191015 | A1 * | 7/2014 | Shelton, IV | A61B 34/70 227/178.1 |
| 2015/0297228 | A1 | 10/2015 | Huitema et al. | |
| 2016/0058450 | A1 * | 3/2016 | Shelton, IV | A61B 17/07207 227/176.1 |
| 2016/0361126 | A1 | 12/2016 | Schena et al. | |
| 2017/0020617 | A1 | 1/2017 | Weir et al. | |
| 2017/0027569 | A1 * | 2/2017 | Scheib | A61B 17/068 |
| 2017/0056012 | A1 * | 3/2017 | Harris | A61B 17/068 |
| 2017/0105727 | A1 * | 4/2017 | Scheib | A61B 17/07207 |
| 2017/0105733 | A1 * | 4/2017 | Scheib | A61B 17/105 |
| 2017/0119397 | A1 * | 5/2017 | Harris | A61B 17/105 |
| 2017/0265865 | A1 | 9/2017 | Burbank | |
| 2017/0265954 | A1 | 9/2017 | Burbank et al. | |
| 2017/0333037 | A1 | 11/2017 | Wellman et al. | |
| 2018/0168756 | A1 | 6/2018 | Liao et al. | |
| 2018/0250008 | A1 * | 9/2018 | Shah | A61B 17/07207 |
| 2018/0271608 | A1 | 9/2018 | Ragosta et al. | |
| 2018/0310935 | A1 | 11/2018 | Wixey | |
| 2018/0325606 | A1 | 11/2018 | Weir et al. | |
| 2018/0344419 | A1 | 12/2018 | Dachs, II et al. | |
| 2019/0038371 | A1 | 2/2019 | Wixey et al. | |
| 2019/0076142 | A1 | 3/2019 | Wixey | |
| 2019/0076143 | A1 | 3/2019 | Smith | |
| 2019/0167266 | A1 | 6/2019 | Patel et al. | |
| 2019/0175177 | A1 * | 6/2019 | Hopkins | A61B 17/0644 |
| 2019/0200989 | A1 | 7/2019 | Burbank et al. | |
| 2019/0239967 | A1 | 8/2019 | Ragosta et al. | |
| 2019/0262088 | A1 | 8/2019 | Burbank | |
| 2020/0138529 | A1 | 5/2020 | Ragosta et al. | |
| 2020/0375597 | A1 * | 12/2020 | Shelton, IV | A61B 17/0682 |
| 2020/0397430 | A1 | 12/2020 | Patel et al. | |
| 2020/0405301 | A1 | 12/2020 | Shelton, IV et al. | |
| 2021/0393340 | A1 | 12/2021 | Beckman et al. | |
| 2021/0401433 | A1 | 12/2021 | Freidel et al. | |
| 2022/0218350 | A1 * | 7/2022 | Shelton, IV | A61B 50/20 |
| 2022/0304679 | A1 * | 9/2022 | Bakos | B33Y 80/00 |
| 2022/0304688 | A1 * | 9/2022 | Shelton, IV | A61B 17/07207 |

FOREIGN PATENT DOCUMENTS

| | | |
|---|---|---|
| WO | WO 2015/153642 A1 | 10/2015 |
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |

(56) References Cited

FOREIGN PATENT DOCUMENTS

| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.
International Search Report and Written Opinion dated Dec. 2, 2022 for Application No. PCT/IB2022/057606, 17 pgs.

\* cited by examiner

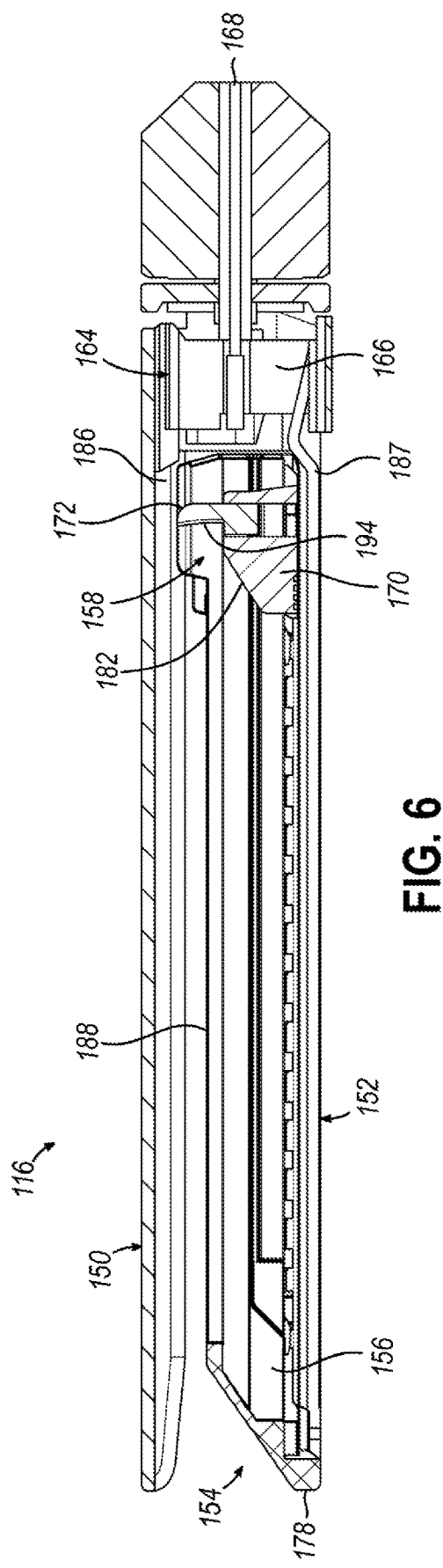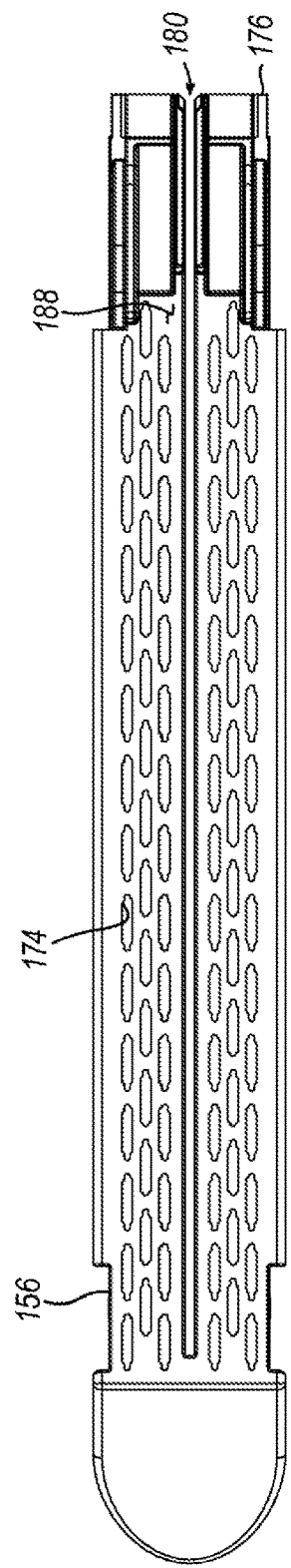
FIG. 6
FIG. 7

FIRING SYSTEM FEATURES FOR SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a side cross-sectional view of the end effector of FIG. 4, where the end effector includes a staple cartridge;

FIG. 7 depicts a top view of a deck of the staple cartridge of FIG. 6;

Figure 1:
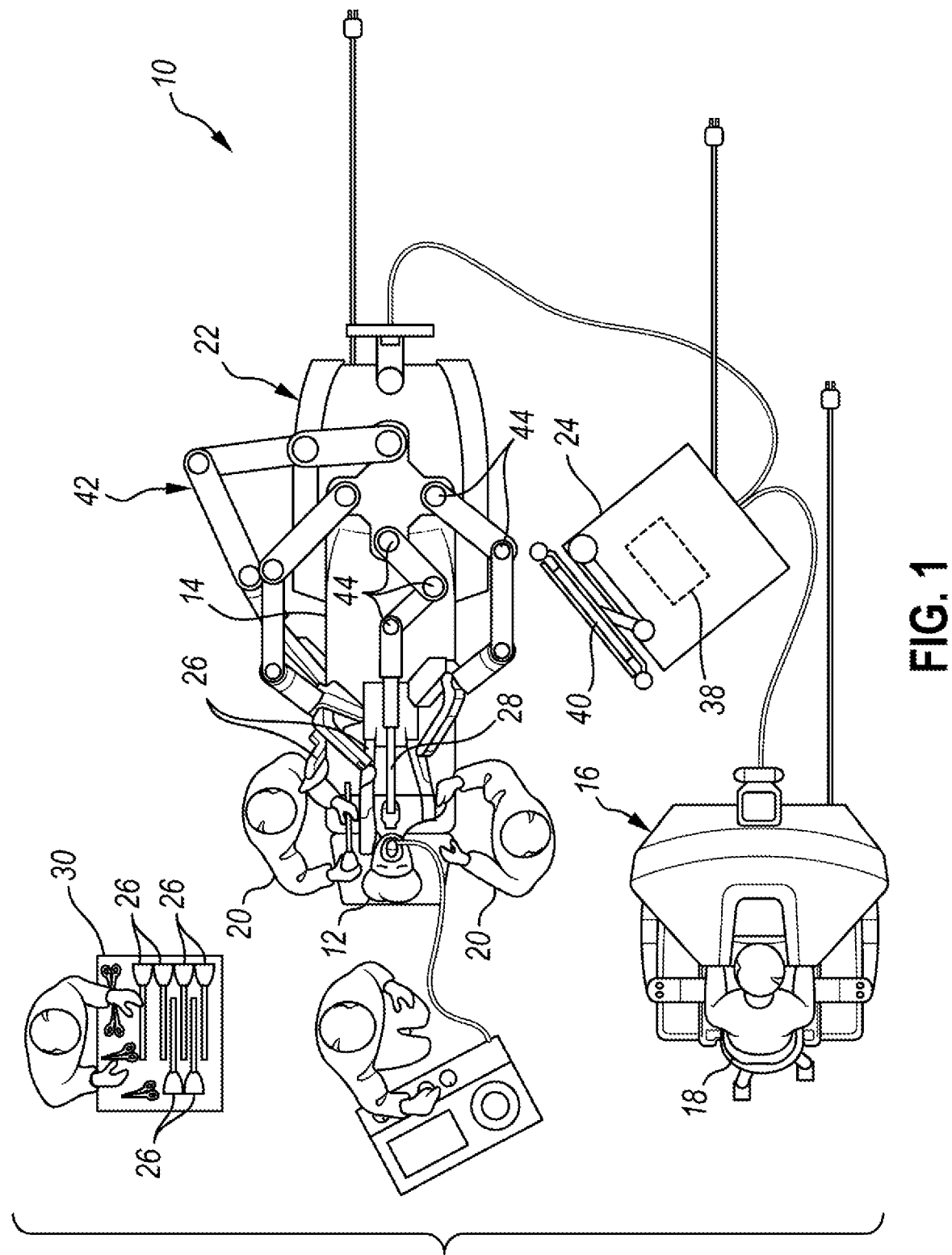
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. EXEMPLARY ROBOTIC SURGICAL SYSTEM

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018; U.S. Pub. No. 2018/0325606, entitled "Systems and Methods for Operating an End Effector," published Nov. 15, 2018; U.S. Pub. No. 2019/0200989, entitled "Stapler Reload Detection and Identification," published Jul. 4, 2019; U.S. Pub. No. 2019/0239967, entitled "Stapler Beam Architecture," published Aug. 8, 2019; U.S. Pub. No. 2019/0262088, entitled "Robotic Surgical Stapler Assembly Configured to Use Stapler Reload," published Aug. 29, 2019; U.S. Pub. No. 2019/0239877, entitled "Wrist Architecture," published Aug. 8, 2019; U.S. Pub. No. 2019/0201150, entitled "Push-Pull Surgical Instrument End Effector Actuation Using Flexible Tension Member," published Jul. 4, 2019; U.S. Pub. No. 2019/0282233, entitled "Stapler Cartridge With an Integral Knife," published Sep. 19, 2019; U.S. Pub. No. 2019/0262088, entitled "Robotic Surgical Stapler Assembly Configured to Use Stapler Reload," published Aug. 29, 2019; U.S. Pub. No. 2020/0138529, entitled "Locking System for Medical Device Drive System," published May 7, 2020; and/or U.S. Pub. No. 2020/0397430, entitled "Surgical Instrument With Lockout Mechanism," published Dec. 24, 2020. The disclosure of each of the above-cited U.S. patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
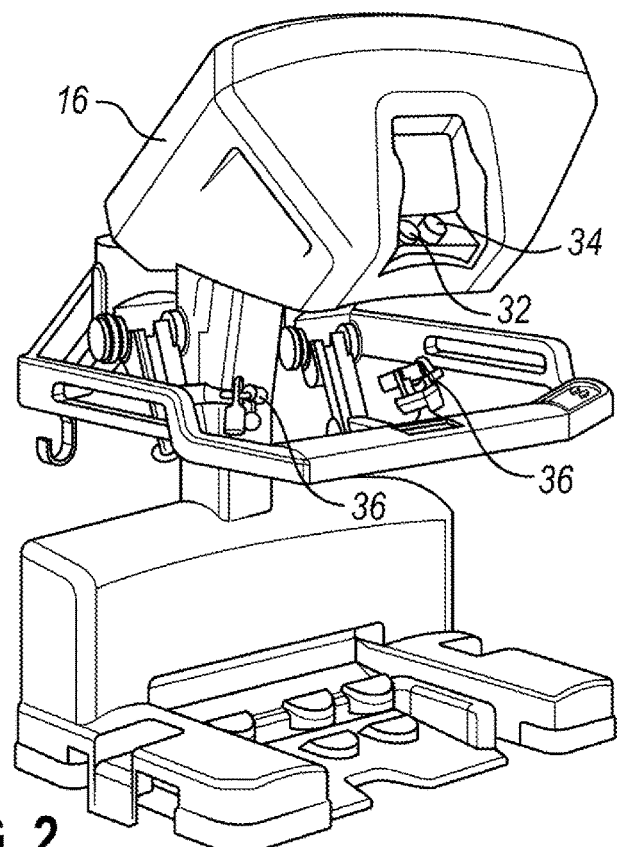
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
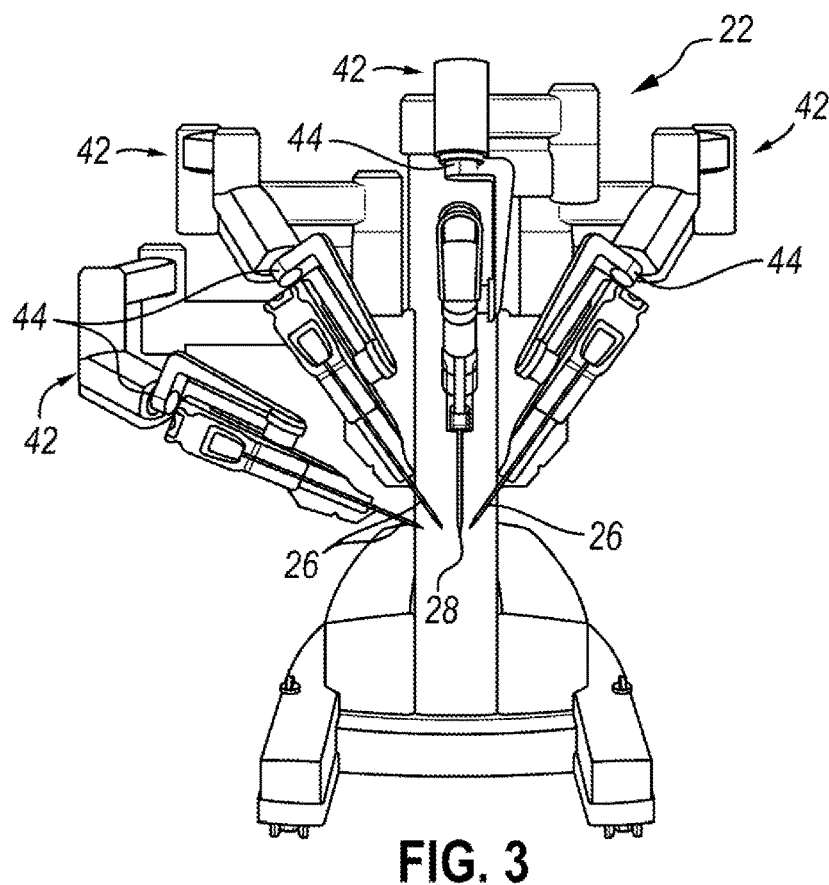
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
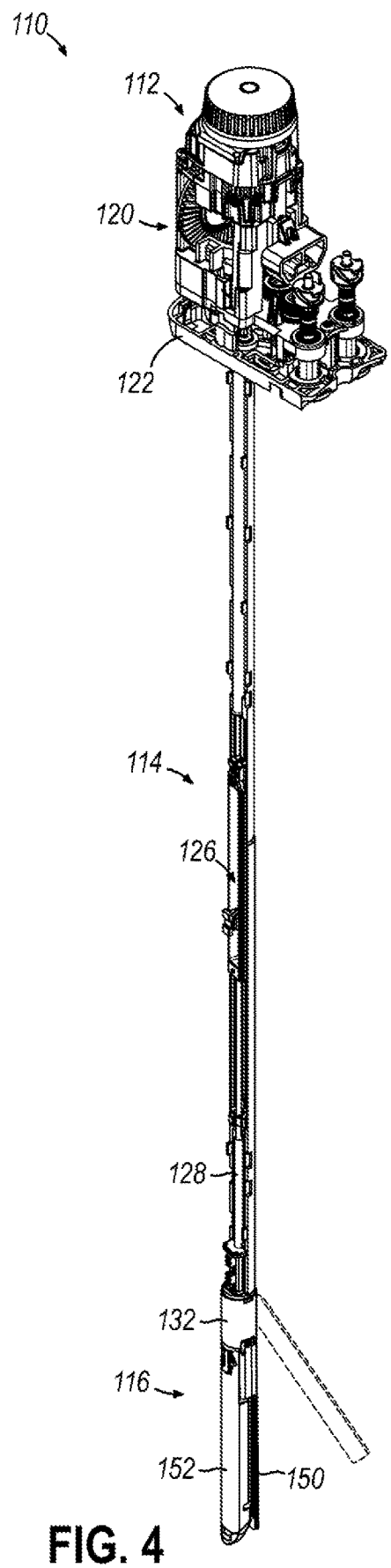
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
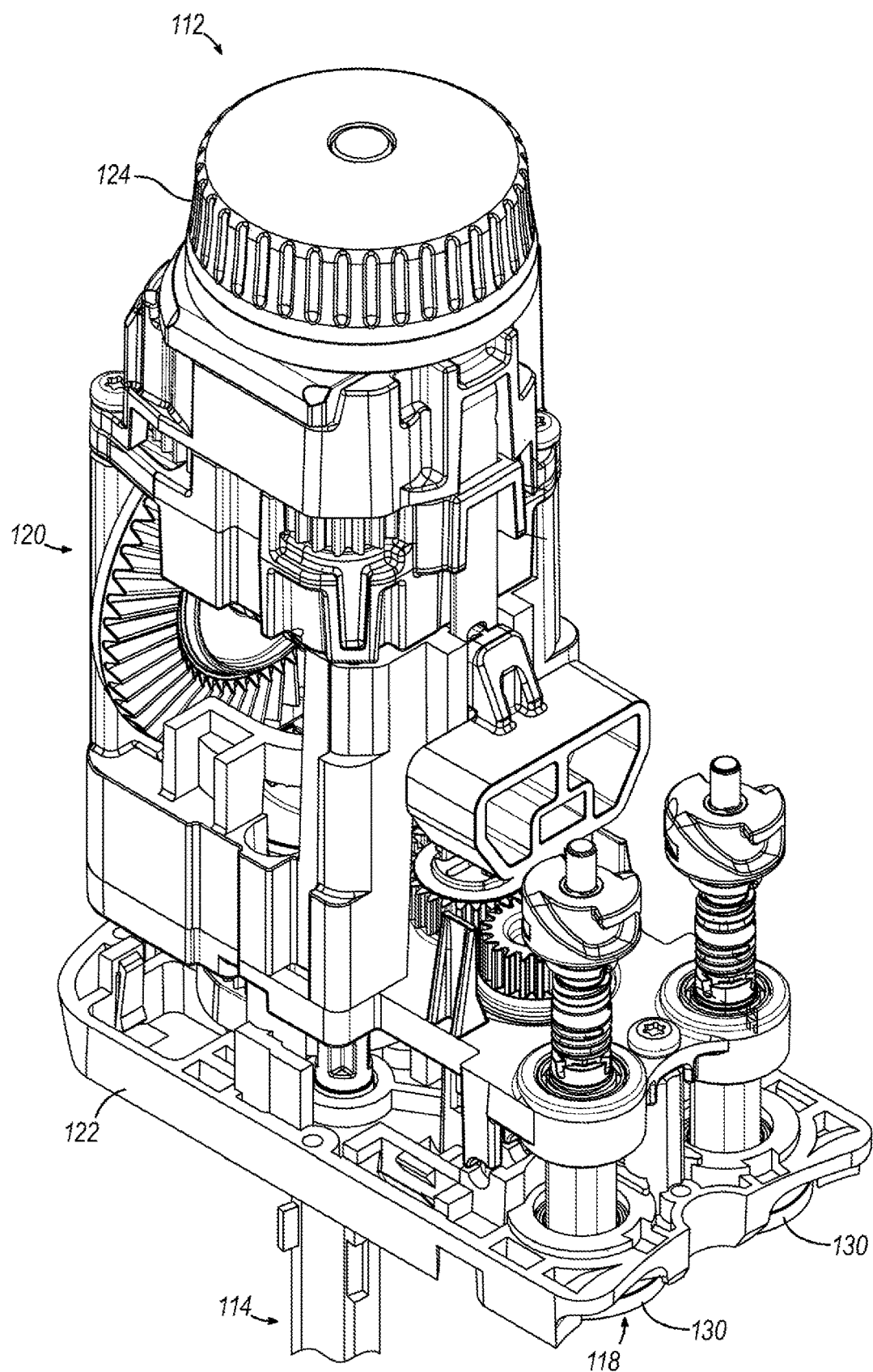
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
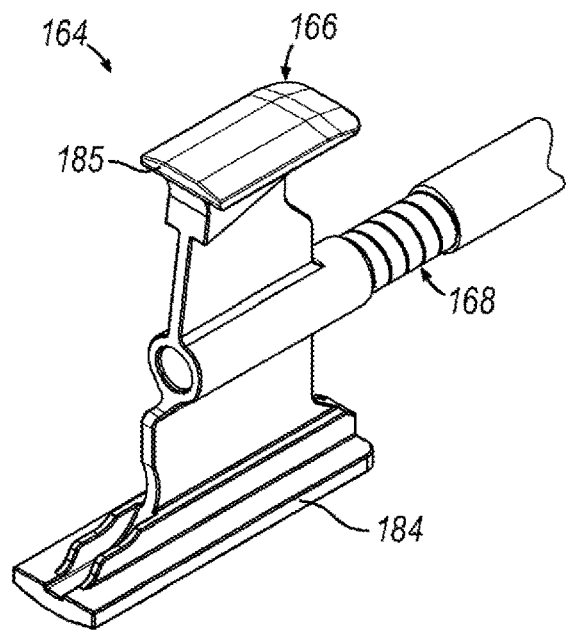
FIG. 8 depicts a driving assembly configured for use with the staple cartridge of FIG. 7.
Figure 9:
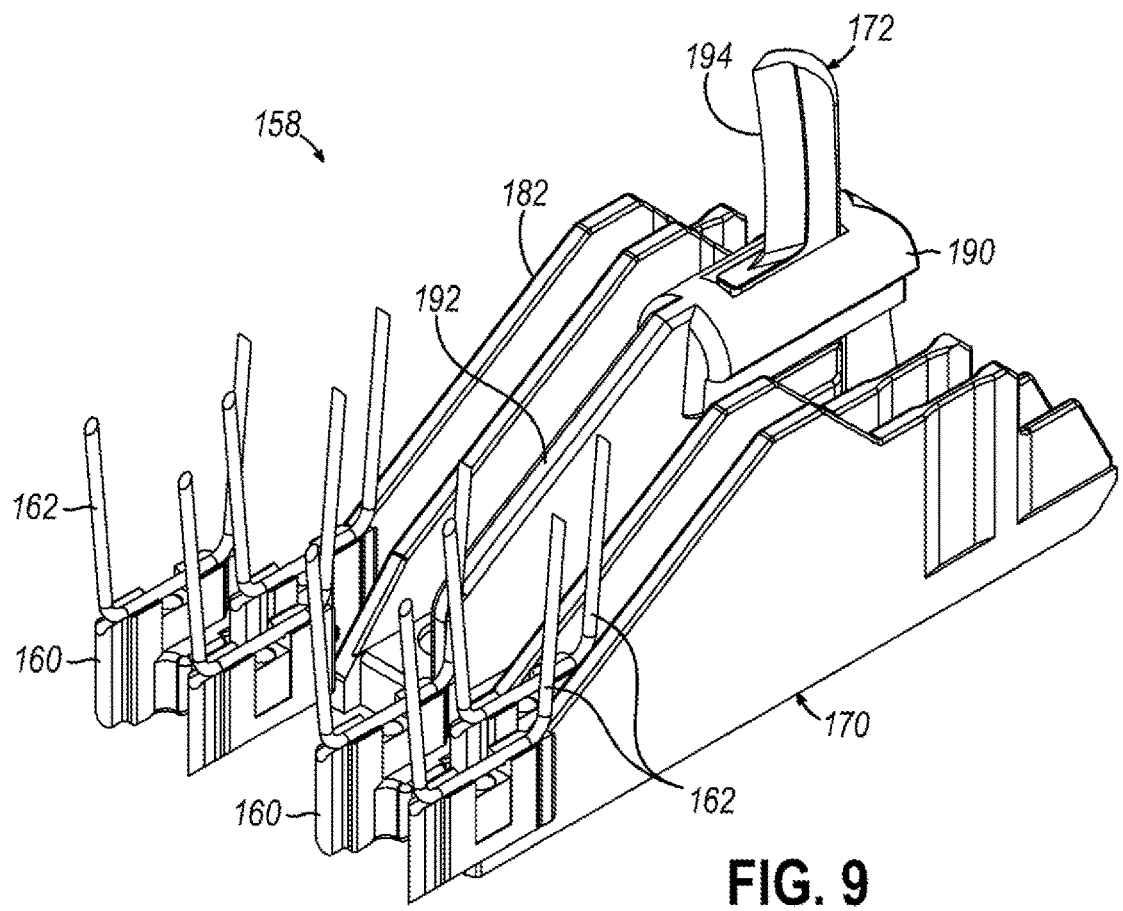
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a staple actuator in the form of a wedge sled (170) (also referred to as a staple pushing shuttle), and a knife member (172).

FIG. 7 shows a top view of staple cartridge body (156). Staple cartridge body (156) includes an array of staple accommodating apertures (174) (also known as "openings") extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
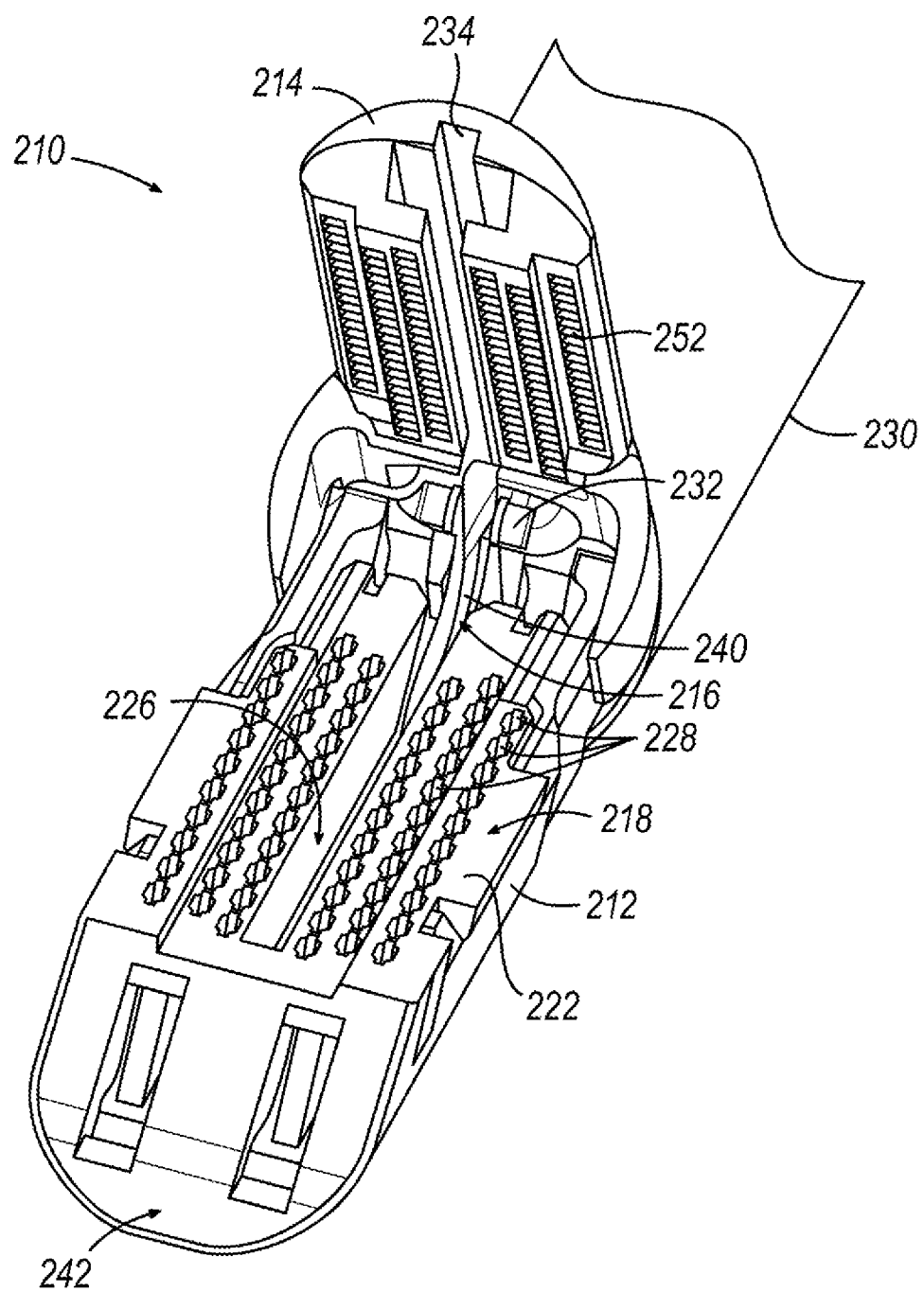
FIG. 10 depicts a second exemplary end effector that may be configured for use with the robotic surgical system of FIG. 1.
Figure 11:
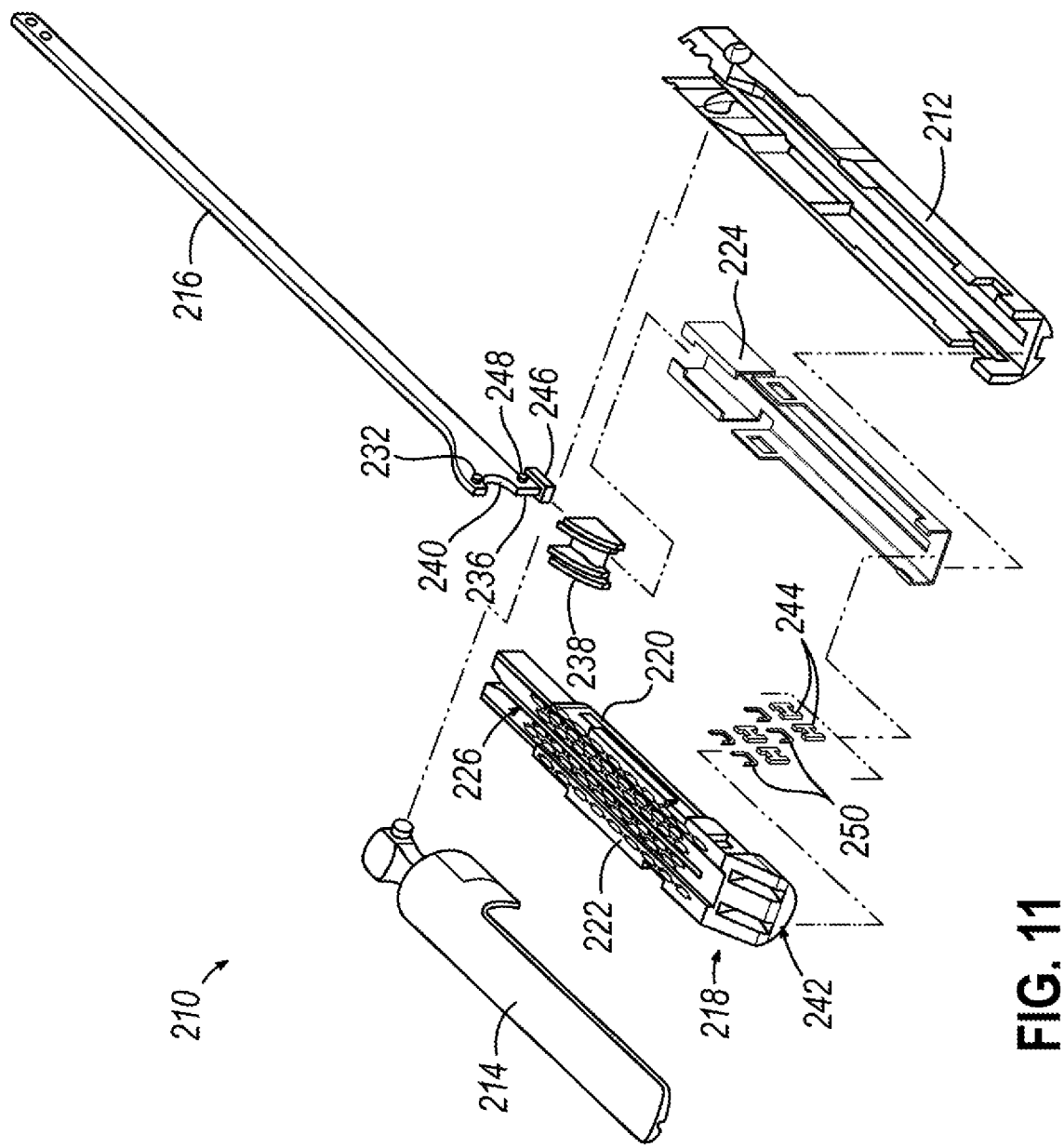
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,497,494 on Nov. 15, 2022, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a staple actuator in the form of a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, issued as U.S. Pat. No. 11,896,202 on Feb. 13, 2024, the disclosure of which is hereby incorporated by reference herein in its entirety.

It will be appreciated that any one or more of the teachings described below may be combined with any one or more of the teachings described above in connection with FIGS. 1-11.

II. EXEMPLARY FIRING SYSTEM FEATURES FOR SURGICAL STAPLER

In some instances, it may be desirable to provide one or more components of the firing system of an end effector (116, 210), such as one or more of staple cartridge (154, 218), wedge sled (170, 238), and/or staple drivers (160, 244) with features to improve the deployment of staples (162, 250) and/or the severing of tissue. More particularly, such features may be configured to assist in minimizing failure of staple cartridge (154, 218) and/or malformation of staples (162, 250), such as by minimizing undesirable rolling of staple drivers (160, 244) when cammingly contacted by wedge sled (170, 238). Each of the staple cartridges (310, 410, 510, 610, 710, 810, 910) described below provides one or more of these functionalities.

A. First Alternative Staple Cartridge with Staple Driver Assemblies

FIGS. 12-16 show an exemplary staple cartridge (310) for use with either end effector (116, 210) described above. Staple cartridge (310) is similar to staple cartridge (154) described above except as otherwise described below. In this regard, staple cartridge (310) includes a staple cartridge body (312) that houses wedge sled (170) (FIGS. 19A-19C). Staple cartridge body (312) includes a proximal end (314) and a distal end (not shown), and further includes an array of staple accommodating apertures (also referred to as "staple apertures") (316a, 316b, 316c) extending through an upper deck (318) of staple cartridge body (312). A vertical slot (319), configured to accommodate a knife member (not shown), such as knife member (172), extends through part of staple cartridge (310). Staple cartridge body (312) is also configured to house a plurality of staple driver assemblies (320, 322, 324a, 324b, 325a, 325b, 326, 328a, 328b) (FIGS. 13-21) in a variety of arrangements, and to house a plurality of staples (not shown), such as staples (162, 250).

In the example shown, staple apertures (316a, 316b, 316c) are arranged in three longitudinal rows on each side of vertical slot (319). More particularly, staple apertures (316a, 316b, 316c) are arranged in a longitudinal row of laterally inner staple apertures (316a), a longitudinal row of laterally intermediate staple apertures (316b), and a longitudinal row of laterally outer staple apertures (316c) on each side of vertical slot (319). In the present version, staple apertures (316a, 316b, 316c) are arranged symmetrically relative to vertical slot (319) and are each oriented substantially parallel thereto, with laterally outer staple apertures (316c) aligned in the lateral direction with respective laterally inner staple apertures (316a), and with laterally intermediate staple apertures (316b) offset from but overlapping in the lateral direction with laterally inner and outer staple apertures (316a, 316c). As shown, the proximal-most laterally inner staple apertures (316a) on each side of vertical slot (319) are aligned with each other in the lateral direction, and are positioned more proximally than the proximal-most laterally intermediate and outer staple apertures (316b, 316c). However, it will be appreciated that staple apertures (316a, 316b, 316c), including the proximal-most laterally inner staple apertures (316a), may be configured and/or arranged in any suitable manner, as described in greater detail below.

Figure 12:
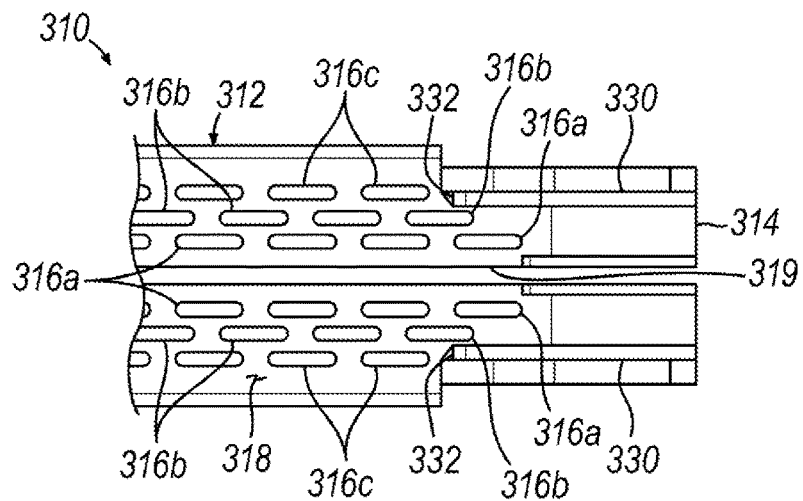
FIG. 12 depicts a partial top view of another exemplary staple cartridge having a plurality of staple apertures and a laterally-opposed pair of proximal tissue stops, with the proximal-most staple apertures positioned proximally of the distal ends of the tissue stops.

As shown in FIG. 12, staple cartridge body (312) also includes a laterally-opposed pair of tissue stops (330) protruding upwardly from a proximal portion of upper deck (318) and terminating distally at respective distal ends (332). Tissue stops (330) may be configured to prevent or otherwise limit the ability of tissue to extend proximally past the respective distal ends (332), such as for assisting in preventing such tissue from being severed too far proximally to receive staples (162, 250) for proper sealing. In this regard, the proximal-most laterally inner staple apertures (316a) are each positioned substantially entirely proximally of the distal end (332) of the respective tissue stop (330), such that the corresponding staples (162, 250) deployed from proximal-most laterally inner staple apertures (316a) are likewise positioned proximally of the distal end (332) of the respective tissue stop (330). Such positioning of proximal-most laterally inner staple apertures (316a) relative to tissue stops (330) may assist in providing proper sealing of the severed tissue, particularly in cases where a portion of the tissue inadvertently extends slightly proximally of the distal end (332) of one or both tissue stops (330).

i. Exemplary Staple Driver Assembly Arrangements

FIGS. 13-16 show various arrangements of staple driver assemblies (320, 322, 324a, 324b, 325a, 325b, 326, 328a, 328b) that may be housed within staple cartridge body (312) and aligned below (e.g., in the transverse direction) one or more corresponding staple apertures (316a, 316b, 316c) for deploying staples (162, 250) therethrough.

Figure 13:
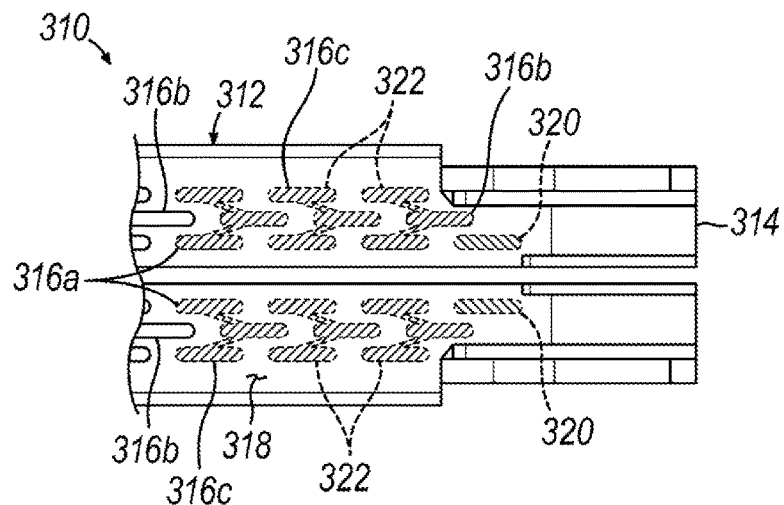
FIG. 13 depicts a partial top view of the staple cartridge of FIG. 12, schematically showing a first arrangement of staple driver assemblies positioned below corresponding staple apertures.

FIG. 13 shows a pair of single-staple driver assemblies (320) aligned below corresponding proximal-most laterally inner staple apertures (316a), and further shows a plurality of triple-staple driver assemblies (322) aligned below corresponding sets of three neighboring staple apertures (316a, 316b, 316c), each set including a distal, laterally inner staple aperture (316a) aligned in the lateral direction with a distal, laterally outer staple aperture (316c) and overlapping in the lateral direction with a proximal, laterally intermediate staple aperture (316b). Triple-staple driver assembly (322) is described in greater detail below in connection with FIGS. 20-21.

Figure 14:
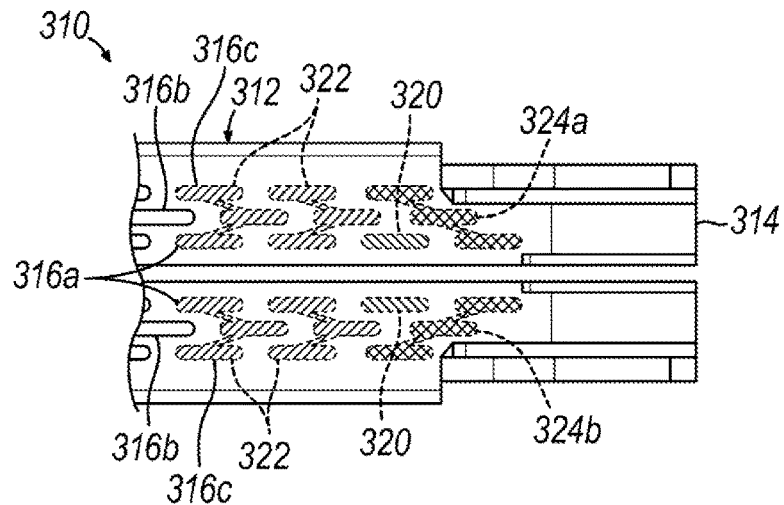
FIG. 14 depicts a partial top view of the staple cartridge of FIG. 12, schematically showing a second arrangement of staple driver assemblies positioned below corresponding staple apertures.

FIG. 14 shows a pair of triple-staple driver assemblies (324a, 324b) aligned below corresponding sets of three neighboring staple apertures (316a, 316b, 316c), each set including the proximal-most laterally inner, intermediate, and outer staple apertures (316a, 316b, 316c). FIG. 14 also shows a pair of single-staple driver assemblies (320) aligned below corresponding laterally inner staple apertures (316a) immediately distal of the respective proximal-most laterally inner staple aperture (316a). FIG. 14 further shows a plurality of triple-staple driver assemblies (322) aligned below corresponding sets of three neighboring staple apertures (316a, 316b, 316c), each set including a distal, laterally inner staple aperture (316a) aligned in the lateral direction with a distal, laterally outer staple aperture (316c) and overlapping in the lateral direction with a proximal, laterally intermediate staple aperture (316b).

Figure 15:
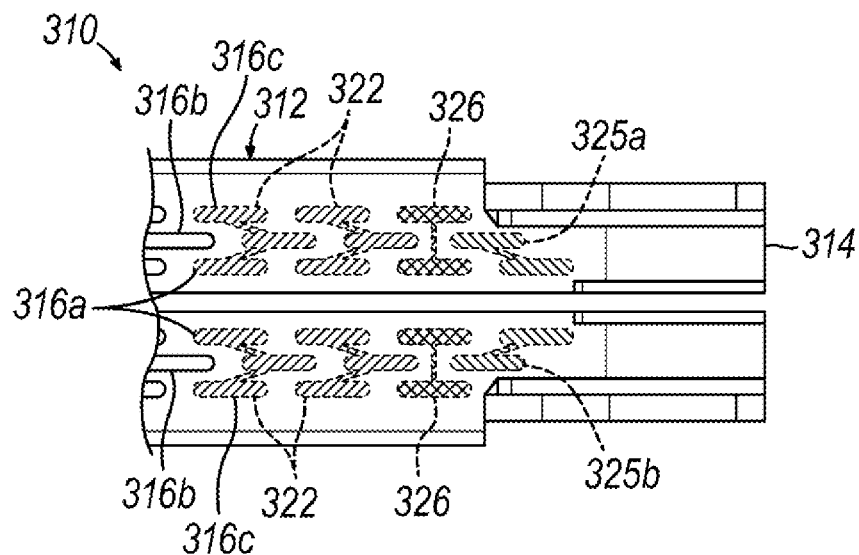
FIG. 15 depicts a partial top view of the staple cartridge of FIG. 12, schematically showing a third arrangement of staple driver assemblies positioned below corresponding staple apertures.

FIG. 15 shows a pair of double-staple driver assemblies (325a, 325b) aligned below corresponding sets of two neighboring staple apertures (316a, 316b), each set including the respective proximal-most laterally inner and intermediate staple aperture (316a, 316b). FIG. 15 also shows a pair of double-staple driver assemblies (326) aligned below corresponding sets of two neighboring staple apertures (316a, 316c), each set including the respective proximal-most laterally outer staple aperture (316c) aligned in the lateral direction with a laterally inner staple aperture (316a). FIG. 15 further shows a plurality of triple-staple driver assemblies (322) aligned below corresponding sets of three neighboring staple apertures (316a, 316b, 316c), each set including a distal, laterally inner staple aperture (316a) aligned in the lateral direction with a distal, laterally outer staple aperture (316c) and overlapping in the lateral direction with a proximal, laterally intermediate staple aperture (316b).

Figure 16:
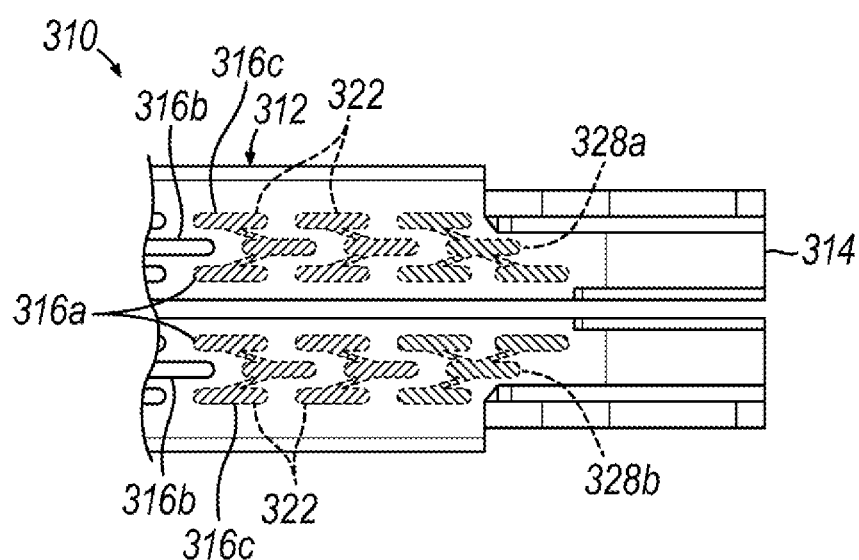
FIG. 16 depicts a partial top view of the staple cartridge of FIG. 12, schematically showing a fourth arrangement of staple driver assemblies positioned below corresponding staple apertures.

FIG. 16 shows a pair of quadruple-staple driver assemblies (328a, 328b) aligned below corresponding sets of four neighboring staple apertures (316a, 316b, 316c), each set including the respective proximal-most laterally inner, intermediate, and outer staple apertures (316a, 316b, 316c), as well as a laterally inner staple aperture (316a) aligned in the lateral direction with the respective proximal-most laterally outer staple aperture (316c). FIG. 16 further shows a plurality of triple-staple driver assemblies (322) aligned below corresponding sets of three neighboring staple apertures (316a, 316b, 316c), each set including a distal, laterally inner staple aperture (316a) aligned in the lateral direction with a distal, laterally outer staple aperture (316c) and overlapping in the lateral direction with a proximal, laterally intermediate staple aperture (316b).

ii. Exemplary Quadruple Staple Driver Assembly

Figure 17:
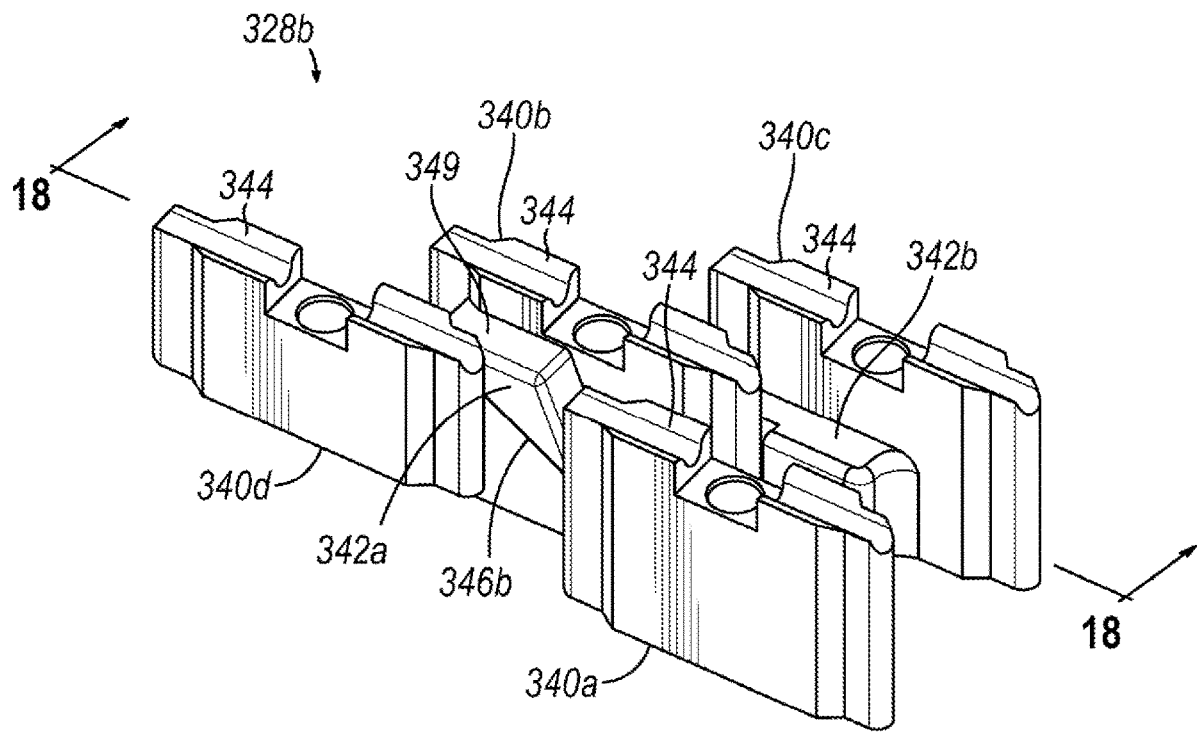
FIG. 17 depicts a perspective view of a quadruple staple driver assembly of the staple cartridge shown in FIG. 16.
Figure 18:
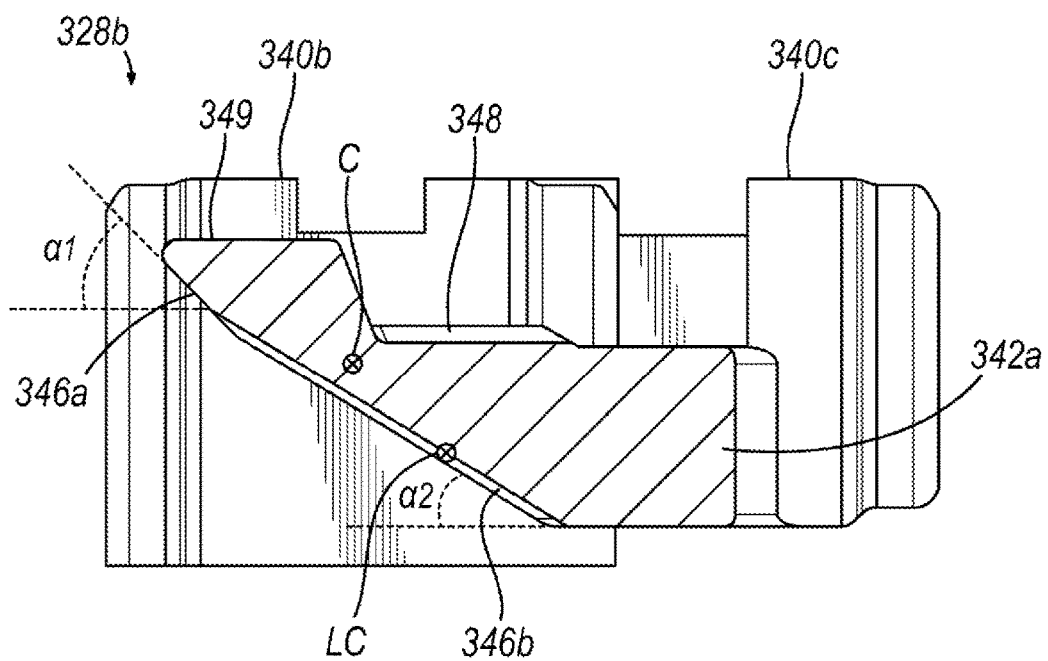
FIG. 18 depicts a cross-sectional view of the quadruple staple driver assembly of FIG. 17, taken along section line 18-18 in FIG. 17.
Figure 19A:
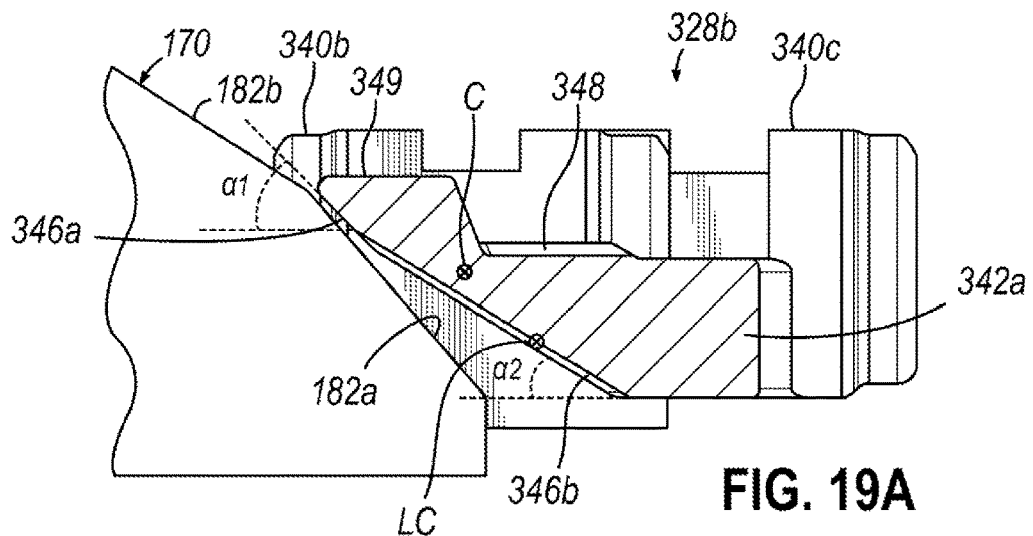
FIG. 19A depicts a cross-sectional view of the quadruple staple driver assembly of FIG. 17, showing a wedge sled of the firing assembly of FIG. 9 in a proximal position relative to the quadruple staple driver assembly.
Figure 19B:
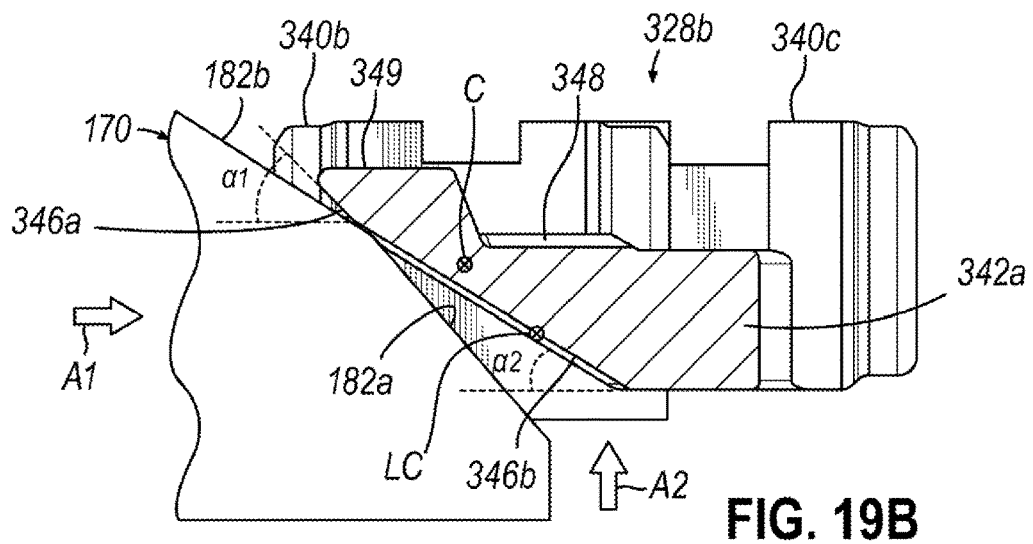
FIG. 19B depicts a cross-sectional view of the quadruple staple driver assembly of FIG. 17, showing the quadruple staple driver assembly lifted by a leading edge of the wedge sled of FIG. 9 during distal translation of the wedge sled.
Figure 19C:
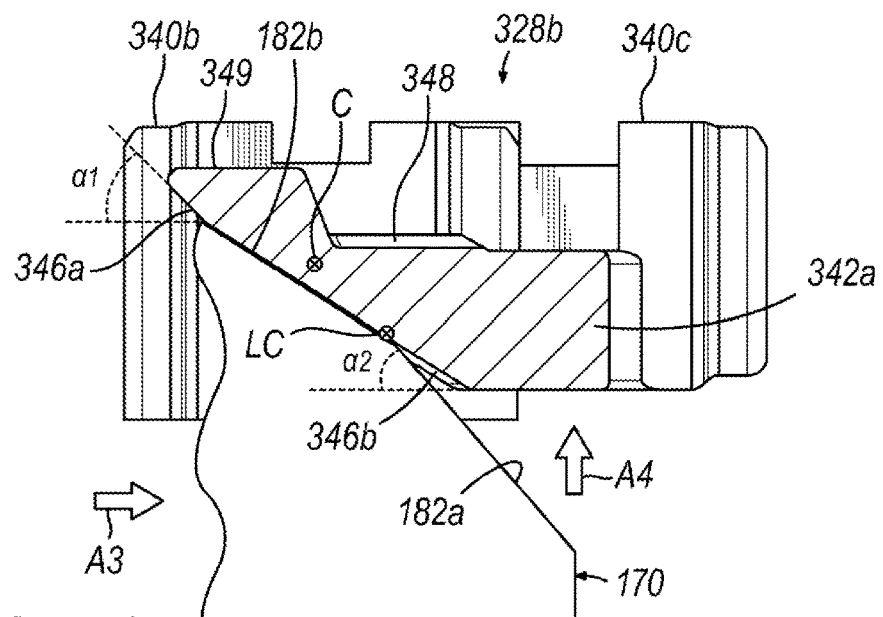
FIG. 19C depicts a cross-sectional view of the quadruple staple driver assembly of FIG. 17, showing the quadruple staple driver assembly lifted by a trailing edge of the wedge sled of FIG. 9 during distal translation of the wedge sled.

Referring now to FIGS. 17 and 18, quadruple staple driver assembly (328b) includes a set of four staple drivers (340a, 340b, 340c, 340d) interconnected by one or more driver cams (342a, 342b) (also referred to as "riggers") extending therebetween. The set of four staple drivers (340a, 340b, 340c, 340d) generally includes a first distally positioned staple driver (340a) and a proximally positioned staple driver (340d) on a first lateral side of first driver cam (342a), an intermediately positioned staple driver (340b) on a second lateral side of first driver cam (342a) and on a first lateral side of second driver cam (342b), and a second distally positioned staple driver (340c) on a second lateral side of second driver cam (342b). Staple drivers (340a, 340b, 340c, 340d) for quadruple driver assembly (328b) are generally positioned such that first and second distally positioned staple drivers (340a, 340c) are aligned in the lateral direction with each other, first and second distally positioned staple drivers (340a, 340c) each overlap in the lateral direction with intermediately positioned staple driver (340b), and proximally positioned staple driver (340d) overlaps in the lateral direction with intermediately positioned staple driver (340b). Each staple driver (340a, 340b, 340c, 340d) further includes at least one longitudinal groove (344) configured to cradle a crown (not shown) of a corresponding one of staples (162, 250).

As best shown in FIG. 18, first driver cam (342a) of quadruple staple driver assembly (328b) presents one or more inclined cam surfaces (346a, 346b) configured to be cammingly contacted by respective ramp portions (182a, 182b) (FIGS. 19A-19C) of wedge sled (170). In the example shown, first driver cam ((342a) includes a proximal cam surface (346a) oriented at a first angle (α1) relative to a horizontal reference plane (e.g., defined by a flat bottom surface of first driver cam (342a) and/or defined by a flat bottom surface of wedge sled (170) or any plane parallel thereto) and configured to be cammingly contacted by a leading ramp portion (182a) of wedge sled (170). First driver cam (342a) also includes a distal cam surface (346b) oriented at a second angle (α2) relative to the horizontal reference plane and configured to be cammingly contacted by a trailing ramp portion (182b) of wedge sled (170). In the present version, first angle (α1) is greater than second angle (α2). It will be appreciated that leading and trailing ramp portions (182a, 182b) of wedge sled (170) may also be oriented at first and second angles (α1, α2), respectively, relative to the horizontal reference plane. In some versions, second angle (α2) may be between approximately 15° and approximately 25°. For example, second angle (α2) may be between approximately 15° and approximately 20°.

In the example shown, first driver cam (342a) includes a distal main body portion (348) and a proximal elevated portion (349) extending upwardly therefrom. In this regard, proximal elevated portion (349) may facilitate connecting proximal staple driver (340d) to intermediate staple driver (340b) at a location above distal main body portion (348), for example. Proximal elevated portion (349) may also provide first driver cam (342a) with an increased cross-sectional area, at least by comparison to that which first driver cam (342a) would have in the absence of proximal elevated portion (349). In some versions, cartridge body (312) may include a clearance feature such as a bore or a recess provided in upper deck (318) for accommodating proximal elevated portion (349) of first driver cam (342a), such as during lifting of first driver cam (342a) via wedge sled (170).

As shown, a distal end of distal cam surface (346b) is positioned substantially distally relative to a centroid (C) of quadruple staple driver assembly (328b) (which may coincide with a center of mass of quadruple staple driver assembly (328b)), such that a majority of the operational loading range of distal cam surface (346b) is distal of centroid (C), and such that the center of contact between distal cam surface (346b) and trailing ramp portion (182b) is distal of centroid (C), at least when the corresponding staples (162, 250) are deployed into forming contact with staple forming pockets (252) on the inner surface of anvil (150, 214) (e.g., when driven upwardly between 0.05 inch and 0.065 inch). More particularly, the apex of the contact between distal cam surface (346b) and trailing ramp portion (182b) when the corresponding staples (162, 250) contact the staple forming pockets (252) may be distal of centroid (C). Such positioning of the center of contact relative to centroid (C), particularly when the corresponding staples (162, 250) contact staple forming pockets (252), may assist in preventing undesirable rolling of quadruple staple driver assembly (328b), such as by allowing the force applied by trailing ramp portion (182b) to distal cam surface (346b) to counteract any moment arm about centroid (C) that might otherwise be applied to quadruple staple driver assembly (328b) by staple forming pockets (252) via the corresponding staples (162, 250). For example, the force applied by trailing ramp portion (182b) to distal cam surface (346b) when the corresponding staples (162, 250) contact the staple forming pockets (252) may be applied to distal cam surface (346b) in a generally distal and upward direction at a load center (LC) distal of centroid (C) to thereby counteract a downwardly-directed moment arm about centroid (C) applied by staple forming pockets (252) via the corresponding staples (162, 250) to quadruple staple driver assembly (328b) at the distal ends of grooves (344) of distal drivers (340a, 340c) to prevent such a moment arm from causing quadruple staple driver assembly (328b) to roll (e.g., clockwise in the frame of reference of FIGS. 18-19C) about its centroid (C). In other words, the geometries of drivers (340a, 340b, 340c, 340d) are selected to balance the moment arms about centroid (C) and thereby resist rolling of quadruple staple driver assembly (328b). Such a configuration may promote proper deployment of staples (162, 250) and avoid jamming of drivers (340a, 340b, 340c, 340d) or damage to staple cartridge (310) which might otherwise result in insufficient tissue sealing. In some versions, a midpoint of distal cam surface (346b) (e.g., halfway between its proximal and distal ends) may be distal of centroid (C).

It will be appreciated that each staple driver (340a, 340b, 340c, 340d) may be unitarily secured to the respective driver cam(s) (342a, 342b) relative to the other staple drivers (340a, 340b, 340c, 340d). It will be further appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein.

Referring now to FIGS. 19A-19C, during firing, wedge sled (170) is driven distally from a proximal position shown in FIG. 19A into upward camming contact with quadruple staple driver assembly (328b) that in turn drive staples (162, 250) out through staple apertures (316a, 316b, 316c) and into forming contact with staple forming pockets (252) on the inner surface of anvil (150, 214). More particularly, leading ramp portion (182a) cammingly engages proximal cam surface (346a) during distal translation of wedge sled (170), as indicated by arrow (A1) in FIG. 19B, to slightly lift quadruple staple driver assembly (328b), as indicated by arrow (A2) in FIG. 19B. Trailing ramp portion (182b) then cammingly engages distal cam surface (346b) during further distal translation of wedge sled (170), as indicated by arrow (A3) in FIG. 19C, to further lift quadruple staple driver assembly (328b), as indicated by arrow (A4) in FIG. 19C. Due to first angle (α1) at which proximal cam surface (346a) is oriented being greater than second angle (α2) at which distal cam surface (346b) is oriented, the initial contact between wedge sled (170) and quadruple staple driver assembly (328b) may occur when wedge sled (170) has been driven relatively more distal than wedge sled (170) would otherwise be driven if first angle (α1) were equal to or less than second angle (α2). Such a delay in the initial contact between wedge sled (170) and quadruple staple driver assembly (328b) may assist in preventing undesirable rolling of quadruple staple driver assembly (328b). It should be understood that cartridge body (312) and anvil (150, 214) are intentionally omitted from the view in FIGS. 19A-19C.

While quadruple staple driver assembly (328b) has been described in connection with FIGS. 17-19C, it will be appreciated that quadruple staple driver assembly (328a) may have a mirrored configuration of that of staple driver assembly (328b).

iii. Exemplary Triple Staple Driver Assembly

Figure 20:
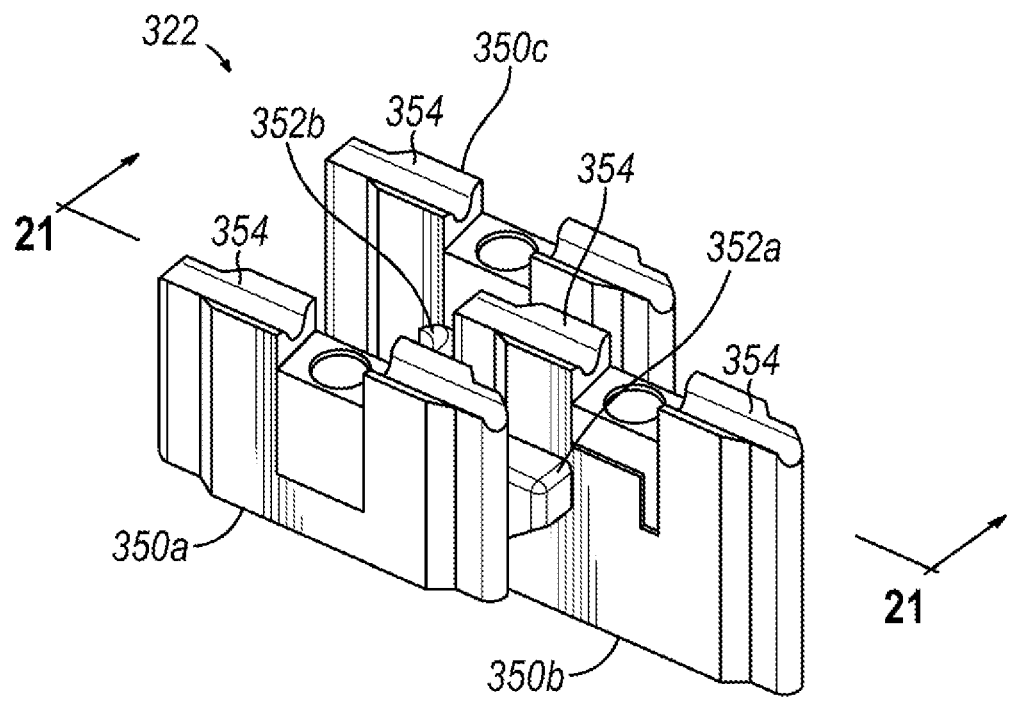
FIG. 20 depicts a perspective view of a triple staple driver assembly of the staple cartridge shown in FIGS. 13-16.
Figure 21:
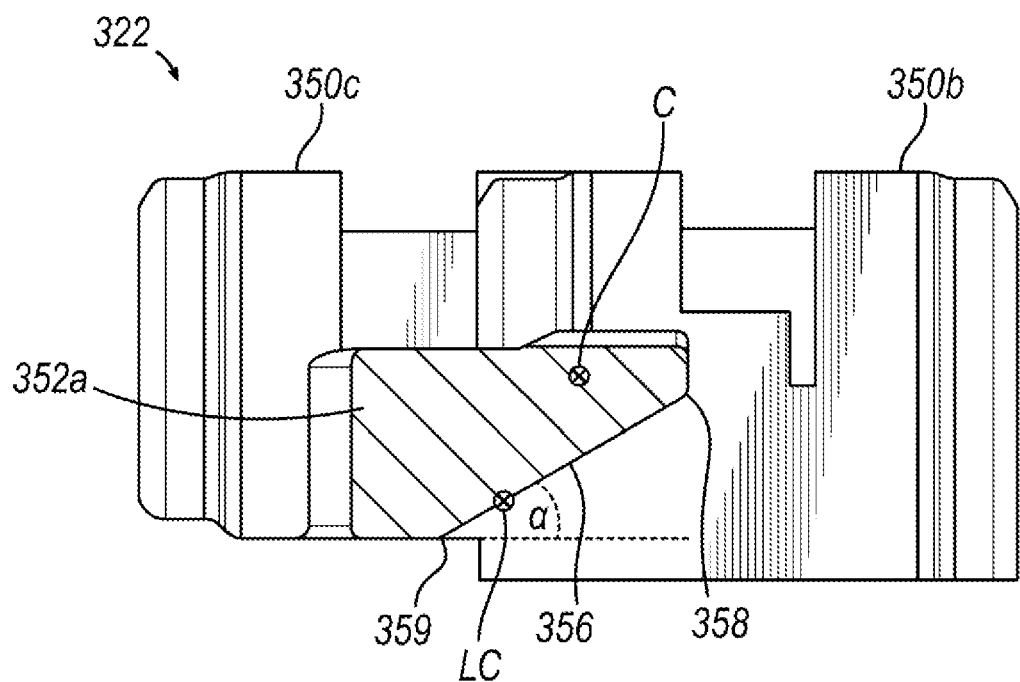
FIG. 21 depicts a cross-sectional view of the triple staple driver assembly of FIG. 20, taken along section line 21-21 in FIG. 20.

Referring now to FIGS. 20 and 21, triple staple driver assembly (322) includes a set of three staple drivers (350a, 350b, 350c) interconnected by one or more driver cams (352a, 352b) (also referred to as "riggers") extending therebetween. The set of three staple drivers (350a, 350b, 350c) generally includes a first distally positioned staple driver (350a) on a first lateral side of first driver cam (352a), a proximally positioned staple driver (350b) on a second lateral side of first driver cam (352a) and on a first lateral side of second driver cam (352b), and a second distally positioned staple driver (350c) on a second lateral side of second driver cam (352b). Staple drivers (350a, 350b, 350c) for triple driver assembly (322) are generally positioned such that first and second distally positioned staple drivers (350a, 350c) are aligned in the lateral direction with each other, and each overlap in the lateral direction with and are equidistantly spaced apart from proximally positioned staple driver (350b). Each staple driver (350a, 350b, 350c) further includes at least one longitudinal groove (354) configured to cradle a crown (not shown) of a corresponding one of staples (162, 250).

As best shown in FIG. 21, first driver cam (352a) of triple staple driver assembly (322) presents an inclined cam surface (356) configured to be cammingly contacted by a respective ramp portion (182, 182a, 182b) (FIGS. 9 and 19A-19C) of wedge sled (170). Cam surface (356) has a proximal end (358) and a distal end (359), and is oriented at an angle ($\alpha$) relative to a horizontal reference plane (e.g., defined by a flat bottom surface of first driver cam (352a) and/or defined by a flat bottom surface of wedge sled (170) or any plane parallel thereto). It will be appreciated that ramp portion (182) of wedge sled (170) may also be oriented at angle ($\alpha$) relative to the horizontal reference plane. In some versions, angle ($\alpha$) may be between approximately 15° and approximately 25°. For example, angle ($\alpha$) may be between approximately 15° and approximately 20°.

As shown, distal end (359) of cam surface (356) is positioned substantially distally relative to a centroid (C) of triple staple driver assembly (322) (which may coincide with a center of mass of triple staple driver assembly (322)), such that a majority of the operational loading range of cam surface (356) is distal of centroid (C), and such that the center of contact between cam surface (356) and ramp portion (182) is distal of centroid (C), at least when the corresponding staples (162, 250) are deployed into forming contact with staple forming pockets (252) on the inner surface of anvil (150, 214) (e.g., when driven upwardly between 0.05 inch and 0.065 inch). More particularly, the apex of the contact between cam surface (356) and ramp portion (182) when the corresponding staples (162, 250) contact the staple forming pockets (252) may be distal of centroid (C). Such positioning of the center of contact relative to centroid (C), particularly when the corresponding staples (162, 250) contact staple forming pockets (252), may assist in preventing undesirable rolling of triple staple driver assembly (322), such as by allowing the force applied by ramp portion (182) to cam surface (356) to counteract any moment arm about centroid (C) that might otherwise be applied to triple staple driver assembly (322) by staple forming pockets (252) via the corresponding staples (162, 250). For example, the force applied by ramp portion (182) to cam surface (356) when the corresponding staples (162, 250) contact the staple forming pockets (252) may be applied to cam surface (356) in a generally distal and upward direction at a load center (LC) distal of centroid (C) to thereby counteract a downwardly-directed moment arm about centroid (C) applied by staple forming pockets (252) via the corresponding staples (162, 250) to triple staple driver assembly (322) at the distal ends of grooves (354) of distal drivers (350a, 350c) to prevent such a moment arm from causing triple staple driver assembly (322) to roll (e.g., counterclockwise in the frame of reference of FIG. 21) about its centroid (C). In other words, the geometries of drivers (350a, 350b, 350c) are selected to balance the moment arms about centroid (C) and thereby resist rolling of triple staple driver assembly (322). Such a configuration may promote proper deployment of staples (162, 250) and avoid jamming of drivers (350a, 350b, 350c) or damage to staple cartridge (310) which might otherwise result in insufficient tissue sealing. In some versions, a midpoint of cam surface (356) (e.g., halfway between proximal and distal ends (358, 359)) may be distal of centroid (C).

It will be appreciated that load center (LC) may be distal relative to centroid (C) since there are two distal staples (162, 250) deployed by distal drivers (350a, 350c) and one proximal staple (162, 250) deployed by proximal driver (350b). It will also be appreciated that a percentage of angle ($\alpha$) may induce a clockwise rotation of triple staple driver assembly (322) about centroid (C) during camming engagement between cam surface (356) and ramp portion (182) that is substantially equal to and opposite the counterclockwise rotation of triple staple driver assembly (322) about centroid (C) induced by the two distal staples (162, 250). Such balancing of the clockwise and counterclockwise rotations may prevent triple staple driver assembly (322) from rotating. In this regard, each staple (162, 250) may require between approximately 1.0 lb. and approximately 3.0 lbs. (e.g., between approximately 1.5 and approximately 2.5 lbs.) to form, such that the total load on triple staple driver assembly (322) may be between approximately 3 lbs. and approximately 9 lbs. in the vertical direction. In cases where wedge sled (170) presents leading and trailing ramp portions (182a, 182b), the non-forming initial raising of triple staple driver assembly (322) by leading ramp portion (182a) may be effectively between approximately 0.5 lb. and approximately 1.0 lb., and second angle ($\alpha 2$) of trailing ramp portion (182b) may be between approximately 15° and approximately 25° (e.g., between approximately 15° and approximately 20°), such that the longitudinal load on wedge sled (170) to generate the vertical force may be between approximately 2 lbs. and approximately 4 lbs. Load center (LC) may be between approximately 0.025 inch and approximately 0.1 inch below centroid (C) causing a moment arm of approximately 0.1 in-lb. in the clockwise direction and the formation of the distal staples (162, 250) causing a moment arm of approximately 0.19 in-lb. in the counterclockwise direction. Any remaining moment arms acting upon triple staple driver assembly (322) to resist rolling of triple staple drive assembly (322) may be caused by the adjacent support walls of staple cartridge body (312). Thus, decreasing the moment arms that the adjacent support walls of staple cartridge body (312) resist may decrease the risk of triple staple driver assembly (322) rolling.

In cases where wedge sled (170) presents leading and trailing ramp portions (182a, 182b), it will be appreciated that the apex of the contact between cam surface (356) and ramp portions (182a, 182b) when the corresponding staples (162, 250) contact the staple forming pockets (252) may be along trailing ramp portion (182b). Moreover, the position of this apex may be at least partially defined by the orientation(s) of ramp portion(s) (182, 182*a*, 182*b*) of wedge sled (170). For example, a change in the orientation(s) of ramp portion(s) (182, 182*a*, 182*b*) from that shown may shift the apex. In such cases, centroid (C) may be shifted to be proximal of the apex.

It will be appreciated that each staple driver (350*a*, 350*b*, 350*c*) may be unitarily secured to the respective driver cam(s) (352*a*, 352*b*) relative to the other staple drivers (350*a*, 350*b*, 350*c*). It will be further appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein.

B. Second Alternative Staple Cartridge with Offset Proximal Apertures

Figure 22:
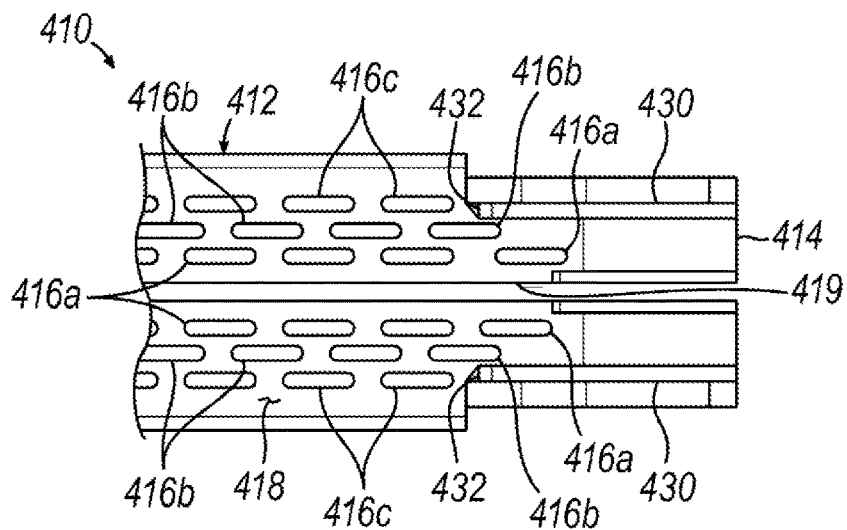
FIG. 22 depicts a partial top view of another exemplary staple cartridge having a plurality of staple apertures and a laterally-opposed pair of proximal tissue stops, with the proximal-most staple apertures positioned proximally of the distal ends of the tissue stops and offset from each other.
Figure 23:
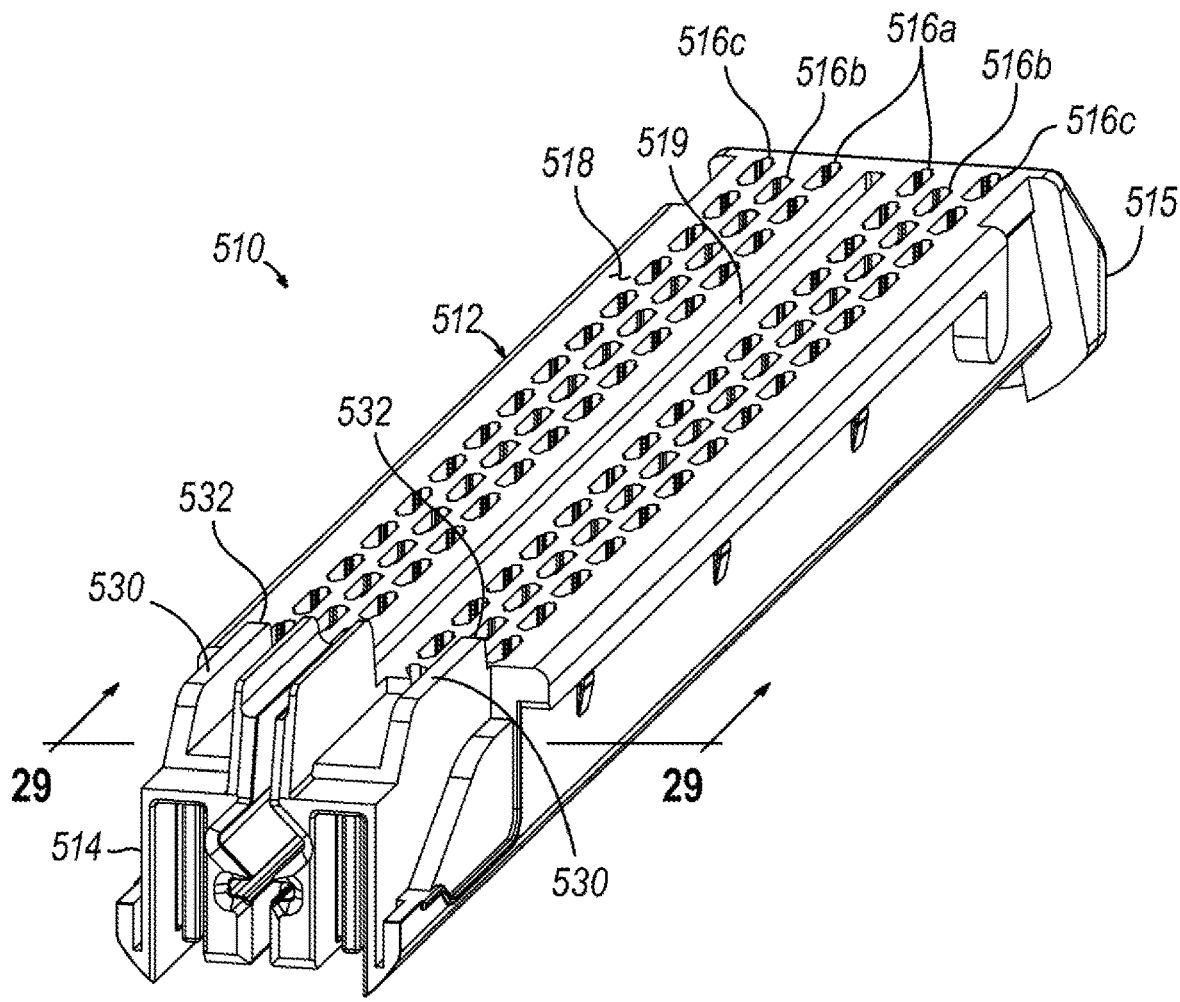
FIG. 23 depicts a perspective view of another exemplary staple cartridge having a diamond-shaped orifice for accommodating a push rod of the driving assembly shown in FIG. 8 and/or a guide member of the firing assembly shown in FIG. 9.
Figure 24:
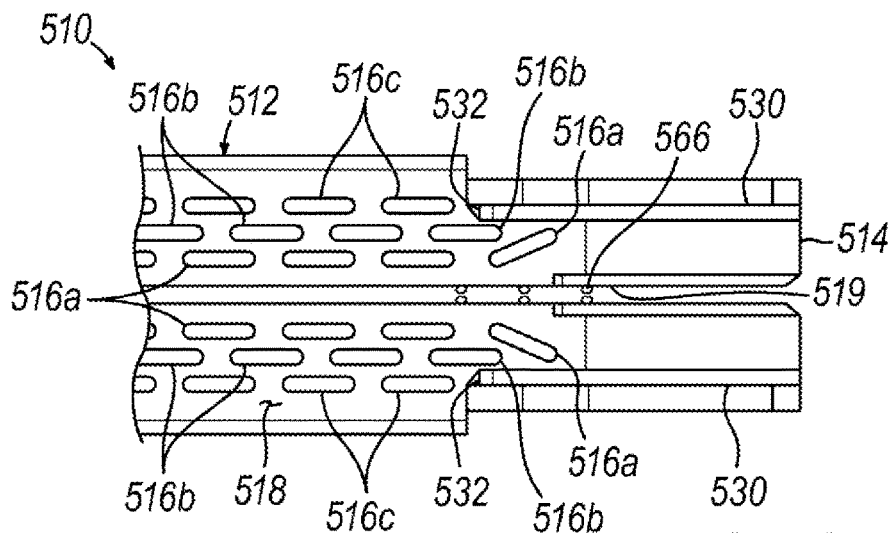
FIG. 24 depicts a partial top view of the staple cartridge of FIG. 23 having a plurality of staple apertures and a laterally-opposed pair of proximal tissue stops, with the proximal-most staple apertures positioned proximally of the distal ends of the tissue stops.

In some instances, it may be desirable to provide a staple cartridge with staple apertures arranged differently from those described above in connection with FIGS. 12-21. FIG. 22 shows an exemplary staple cartridge (410) for use with either end effector (116, 210) described above that provides such functionalities. Staple cartridge (410) is similar to staple cartridge (310) described above except as otherwise described below. In this regard, staple cartridge (410) includes a staple cartridge body (412) having a proximal end (414) and an array of staple apertures (416*a*, 416*b*, 416*c*) extending through an upper deck (418). A vertical slot (419) extends through part of staple cartridge (410), and a laterally-opposed pair of tissue stops (430) protrude upwardly from a proximal portion of upper deck (418) and terminate distally at respective distal ends (432). The proximal-most laterally inner staple apertures (416*a*) are each positioned substantially entirely proximally of the distal end (432) of the respective tissue stop (420).

In the present version, staple apertures (416*a*, 416*b*, 416*c*) are arranged symmetrically relative to vertical slot (419) with the exception of the proximal-most laterally inner staple apertures (416*a*). As shown, the proximal-most laterally inner staple apertures (416*a*) on each side of vertical slot (419) are offset from each other in the lateral direction. More particularly, the proximal-most laterally inner staple aperture (416*a*) on the righthand side of vertical slot (419) (e.g., above vertical slot (419) in the view of FIG. 22) is positioned more proximally than the proximal-most laterally inner staple aperture (416*a*) on the left-hand side of vertical slot (419) (e.g., below vertical slot (419) in the view of FIG. 22). In some versions, the right-hand ramp portions (182) of wedge sled (170) may be positioned proximally relative to the left-hand ramp portions (182) of wedge sled (170) to accommodate the laterally-offset arrangement of the proximal-most laterally inner staple apertures (416*a*) when wedge sled (170) is at its initial proximal position.

C. Third Alternative Staple Cartridge with Staple Driver Assemblies

In some instances, it may be desirable to provide a staple cartridge with staple apertures and staple drivers configured and/or arranged differently from those described above in connection with FIGS. 12-21. In addition, or alternatively, it may be desirable to provide a staple cartridge with cartridge support features and/or to provide a staple cartridge that is configured to permit the firing member and/or guide member to horizontally stabilize the cartridge body. FIGS. 23-30 show an exemplary staple cartridge (510) for use with either end effector (116, 210) described above that provides such functionalities. Staple cartridge (510) is similar to staple cartridge (310) described above except as otherwise described below. In this regard, staple cartridge (510) includes a staple cartridge body (512) having a proximal end (514) and a distal end (515), and an array of staple apertures (516*a*, 516*b*, 516*c*) extending through an upper deck (518). A vertical slot (519) extends through part of staple cartridge (510), and a laterally-opposed pair of tissue stops (530) protrude upwardly from a proximal portion of upper deck (518) and terminate distally at respective distal ends (532). The proximal-most laterally inner staple apertures (516*a*) are each positioned substantially entirely proximally of the distal end (532) of the respective tissue stop (520). Staple cartridge body (512) is also configured to house a plurality of staple driver assemblies (320, 322, 326, 523*a*, 523*b*, 527*a*, 527*b*, 529*a*, 529*b*) (FIGS. 25-28) in a variety of arrangements, and to house a plurality of staples (not shown), such as staples (162, 250).

Figure 26:
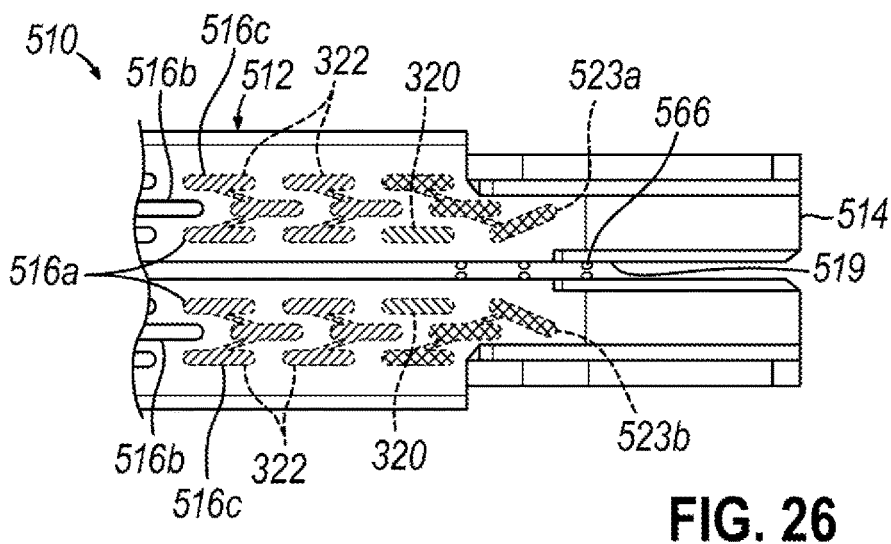
FIG. 26 depicts a partial top view of the staple cartridge of FIG. 23, schematically showing a second arrangement of staple driver assemblies positioned below corresponding staple apertures.

In the present version, staple apertures (516*a*, 516*b*, 516*c*) are each oriented substantially parallel to vertical slot (519) with the exception of the proximal-most laterally inner staple apertures (516*a*). As best shown in FIG. 26, the proximal-most laterally inner staple apertures (516*a*) on each side of vertical slot (519) are each oriented at a same angle relative to vertical slot (519). More particularly, the proximal-most laterally inner staple apertures (516*a*) are each angled laterally outwardly in the proximal direction. Such angling of the proximal-most laterally inner staple apertures (516*a*) may allow the proximal-most laterally inner staple apertures (516*a*) to occupy a relatively footprint in the longitudinal direction, at least by comparison to the proximal-most laterally inner staple apertures (316*a*, 416*a*) described above, without requiring a reduction in the lengths of the proximal-most laterally inner staple apertures (516*a*).

i. Exemplary Staple Driver Assembly Arrangements

FIGS. 25-28 show various arrangements of staple driver assemblies (320, 322, 326, 523*a*, 523*b*, 527*a*, 527*b*, 529*a*, 529*b*) that may be housed within staple cartridge body (512) and aligned below (e.g., in the transverse direction) one or more corresponding staple apertures (516*a*, 516*b*, 516*c*) for deploying staples (162, 250) therethrough.

Figure 25:
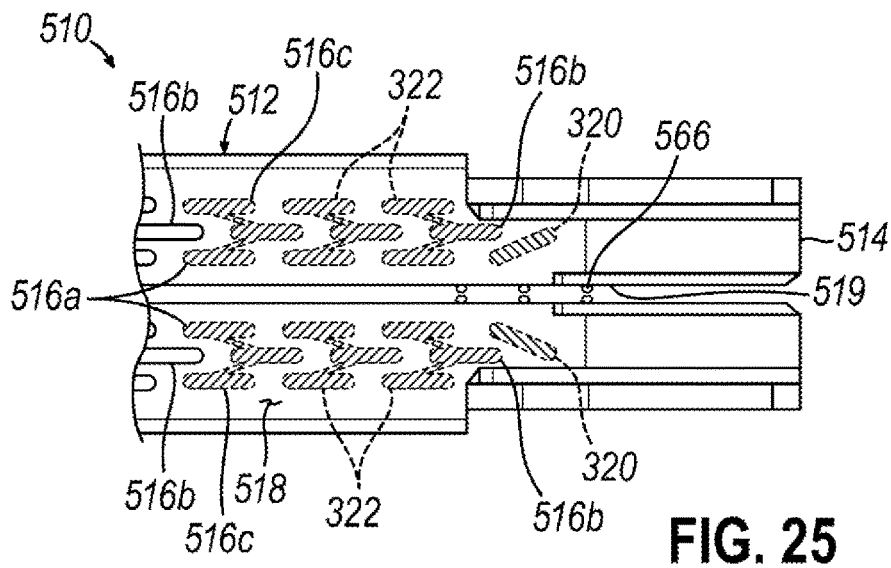
FIG. 25 depicts a partial top view of the staple cartridge of FIG. 23, schematically showing a first arrangement of staple driver assemblies positioned below corresponding staple apertures.

FIG. 25 shows a pair of single-staple driver assemblies (320) aligned below corresponding proximal-most laterally inner staple apertures (516*a*), and further shows a plurality of triple-staple driver assemblies (322) aligned below corresponding sets of three neighboring staple apertures (516*a*, 516*b*, 516*c*), each set including a distal, laterally inner staple aperture (516*a*) aligned in the lateral direction with a distal, laterally outer staple aperture (516*c*) and overlapping in the lateral direction with a proximal, laterally intermediate staple aperture (516*b*).

FIG. 26 shows a pair of triple-staple driver assemblies (523*a*, 523*b*) aligned below corresponding sets of three neighboring staple apertures (516*a*, 516*b*, 516*c*), each set including the proximal-most laterally inner, intermediate, and outer staple apertures (516*a*, 516*b*, 516*c*). FIG. 26 also shows a pair of single-staple driver assemblies (320) aligned below corresponding laterally inner staple apertures (516*a*) immediately distal of the respective proximal-most laterally inner staple aperture (516*a*). FIG. 26 further shows a plurality of triple-staple driver assemblies (322) aligned below corresponding sets of three neighboring staple apertures (516*a*, 516*b*, 516*c*), each set including a distal, laterally inner staple aperture (516*a*) aligned in the lateral direction with a distal, laterally outer staple aperture (516*c*) and overlapping in the lateral direction with a proximal, laterally intermediate staple aperture (516*b*).

Figure 27:
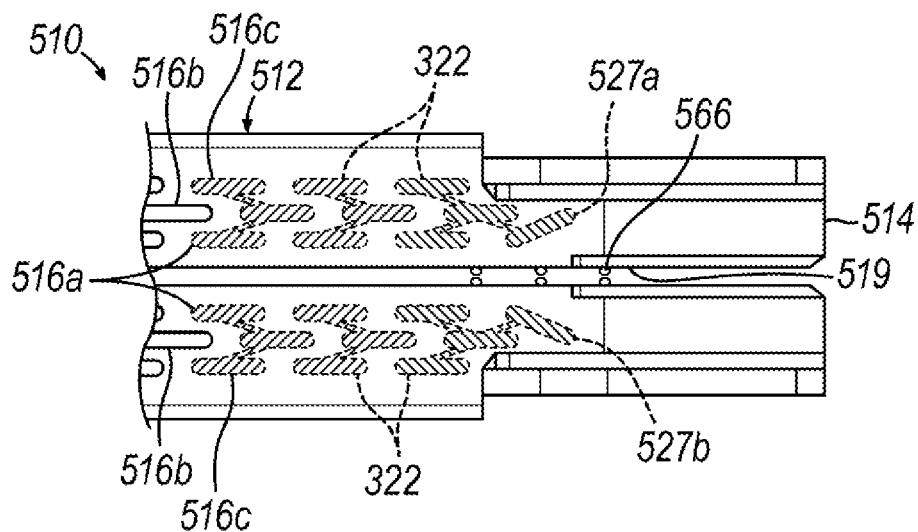
FIG. 27 depicts a partial top view of the staple cartridge of FIG. 23, schematically showing a third arrangement of staple driver assemblies positioned below corresponding staple apertures.

FIG. 27 shows a pair of quadruple-staple driver assemblies (527*a*, 527*b*) aligned below corresponding sets of four neighboring staple apertures (516a, 516b, 516c), each set including the respective proximal-most laterally inner, intermediate, and outer staple apertures (516a, 516b, 516c), as well as a laterally inner staple aperture (516a) aligned in the lateral direction with the respective proximal-most laterally outer staple aperture (516c). FIG. 27 further shows a plurality of triple-staple driver assemblies (322) aligned below corresponding sets of three neighboring staple apertures (516a, 516b, 516c), each set including a distal, laterally inner staple aperture (516a) aligned in the lateral direction with a distal, laterally outer staple aperture (516c) and overlapping in the lateral direction with a proximal, laterally intermediate staple aperture (516b).

Figure 28:
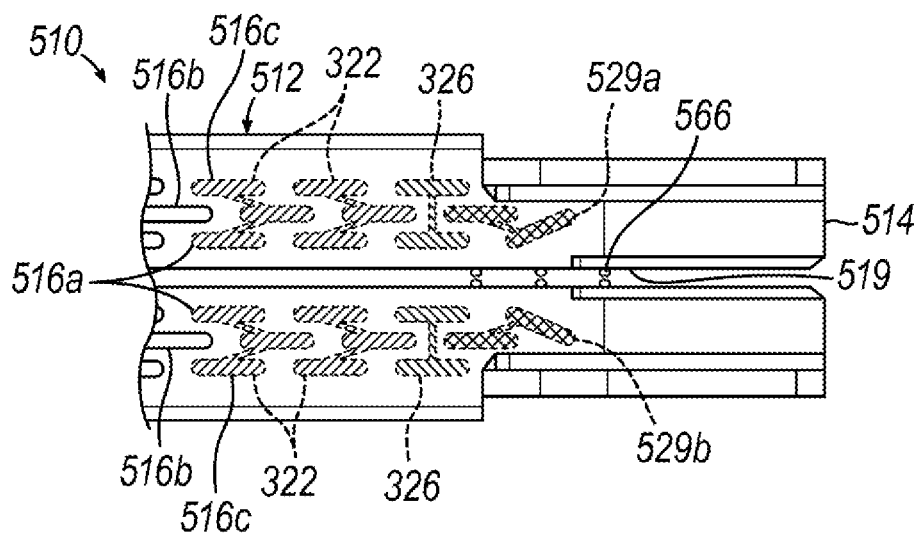
FIG. 28 depicts a partial top view of the staple cartridge of FIG. 23, schematically showing a fourth arrangement of staple driver assemblies positioned below corresponding staple apertures.

FIG. 28 shows a pair of double-staple driver assemblies (529a, 529b) aligned below corresponding sets of two neighboring staple apertures (516a, 516b), each set including the respective proximal-most laterally inner and intermediate staple aperture (516a, 516b). FIG. 28 also shows a pair of double-staple driver assemblies (326) aligned below corresponding sets of two neighboring staple apertures (516a, 516c), each set including the respective proximal-most laterally outer staple aperture (516c) aligned in the lateral direction with a laterally inner staple aperture (516a). FIG. 28 further shows a plurality of triple-staple driver assemblies (322) aligned below corresponding sets of three neighboring staple apertures (516a, 516b, 516c), each set including a distal, laterally inner staple aperture (516a) aligned in the lateral direction with a distal, laterally outer staple aperture (516c) and overlapping in the lateral direction with a proximal, laterally intermediate staple aperture (516b).

ii. Exemplary Diamond-Shaped Cartridge Orifice

Figure 29:
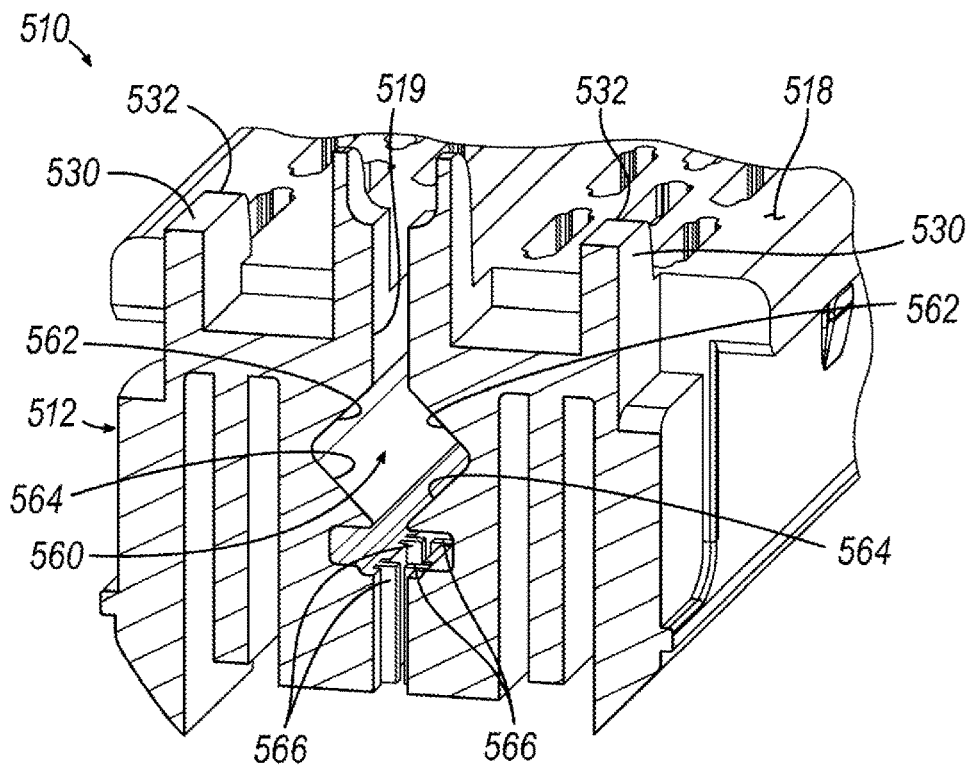
FIG. 29 depicts a cross-sectional perspective view of the staple cartridge of FIG. 23, taken along section line 29-29 in FIG. 23, showing cartridge support features of the staple cartridge extending laterally inwardly from respective sides of a vertical slot of the staple cartridge.
Figure 30:
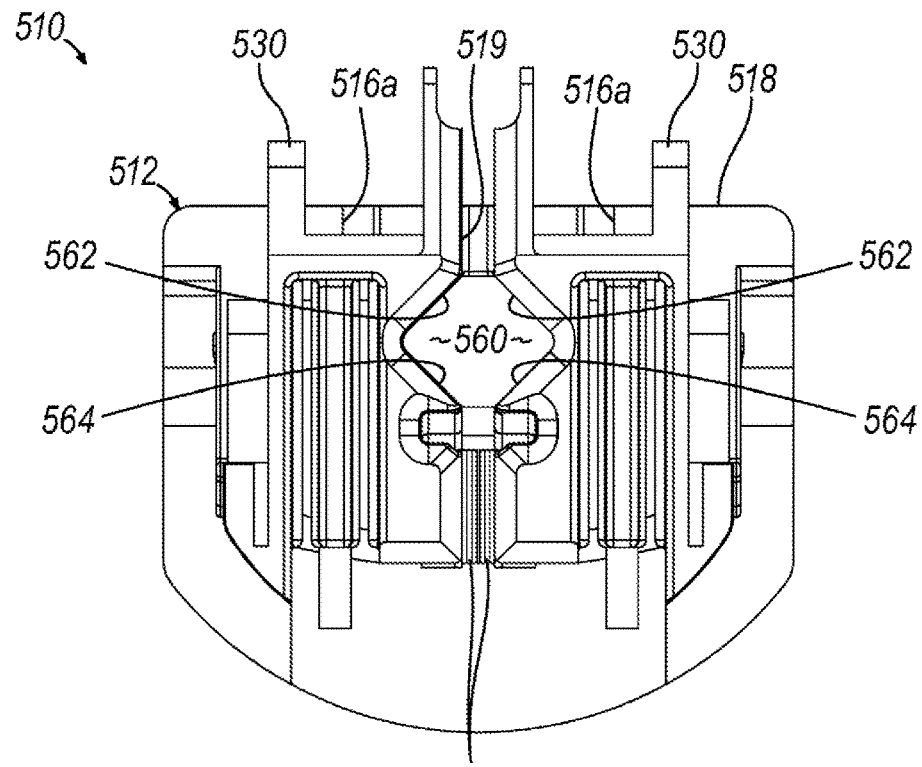
FIG. 30 depicts a rear elevation view of the staple cartridge of FIG. 23.

Referring now to FIGS. 29 and 30, a longitudinal orifice (560), configured to accommodate a firing member (not shown), such as push rod (168), and/or to accommodate a guide member of a wedge sled (not shown), such as guide member (190), extends laterally outwardly from both sides of vertical slot (519). In the example shown, orifice (560) is defined by a laterally-opposed pair of upper flat surfaces (562) extending laterally outwardly and downwardly from upper portions of respective sides of vertical slot (519), and by a laterally-opposed pair of lower flat surfaces (564) extending laterally outwardly and upwardly from lower portions of respective sides of vertical slot (519) to corresponding upper flat surfaces (562). In this manner, orifice (560) may have a generally diamond-shaped cross section, bifurcated by and symmetrical relative to vertical slot (519). In some versions, flat surfaces (562, 564) of orifice (560) may have a uniform length, and each flat surface (562, 564) may be oriented generally perpendicularly relative to each of the adjacent flat surfaces (562, 564).

In some versions, the cross-sectional shape of orifice (560) may be substantially different from that of the firing and/or guide member(s) accommodated by orifice (560). For example, push rod (168) and guide member (190) described above each have generally round and/or circular cross-sectional shapes substantially different from the diamond cross-sectional shape of orifice (560). Moreover, such differently-shaped firing and/or guide member(s) may be sized to contact flat surfaces (562, 564) of orifice (560) at predetermined locations therealong. For example, the rounded and/or circular cross-sectional shapes of push rod (168) and/or guide member (190) may be defined by at least one radius substantially equal to or slightly greater than the shortest distances between a centerpoint of orifice (560) and each of the flat surfaces (562, 564). It will be appreciated that such shortest distances may occur at or near a midpoint of each of the flat surfaces (562, 564). In this manner, the firing and/or guide member(s), such as push rod (168) and/or guide member (190), may contact each flat surface (562, 564) at or near the midpoint thereof while moving longitudinally through staple cartridge (510) to thereby horizontally stabilize cartridge body (512). For example, push rod (168) and/or guide member (190) may inhibit laterally inward deflection (e.g., buckling) of cartridge body (512). In this regard, push rod (168) and/or guide member (190) may urge the corresponding portions of cartridge body (512) on either side of vertical slot (519) toward a substantially vertical orientation by counteracting any laterally-inwardly directed forces that might be applied to such portions of cartridge body (512) during use (e.g., clamping and/or firing).

iii. Exemplary Cartridge Support Ribs

With continuing reference to FIGS. 29 and 30, a plurality of deflectable cartridge support features in the form of laterally-opposed pairs of vertical, flexible ribs (566) extend laterally inwardly from both sides of vertical slot (519). In some versions, each rib (566) may be at least partially defined between generally parallel proximal and distal slots which extend laterally outwardly from the respective side of vertical slot (519) into cartridge body (512). Thus, each rib (566) may be integrally formed with an adjoining portion of cartridge body (512) and cantilevered relative thereto. In the example shown, ribs (566) are arranged in a proximal, lower portion of cartridge body (512), with each rib (566) positioned below orifice (560) and with the distal-most ribs (566) positioned only slightly distally of tissue stops (530).

In the present version, each rib (566) is configured to flex (e.g., bend, swing, and/or fold) in the longitudinal direction (e.g., distally), and is resiliently biased in the longitudinal direction (e.g., proximally) to its unflexed state, as shown in FIGS. 29 and 30. The integrally formed, cantilevered configuration of each rib (566) relative to the adjoining portion of cartridge body (512) may assist in maintaining each rib (566) in its unflexed state in the absence of longitudinally-directed external forces acting upon rib (566).

In the example shown, each rib (566) on each side of vertical slot (519) is aligned with an opposing rib (566) on the opposite side of vertical slot (519) in the lateral direction, such that the laterally inner ends of each laterally-opposed pair of ribs (566) confront and are configured to contact each other to thereby horizontally stabilize cartridge body (512). For example, ribs (566) may inhibit laterally inward deflection (e.g., buckling) of cartridge body (512). In this regard, ribs (566) on each side of vertical slot (519) may each urge the portion of cartridge body (512) on the opposite side of vertical slot (519) toward a substantially vertical orientation by counteracting any laterally-inwardly directed forces that might be applied to such portions of cartridge body (512) during use (e.g., clamping and/or firing). Due to the flexibility of ribs (566) in the longitudinal direction, a portion of a driving assembly (not shown), such as pusher member (166) or vertical rib member (192) of wedge sled (170), may sequentially engage each pair of ribs (566) and urge the respective ribs (566) distally to their flexed states to thereby permit advancement of the driving assembly while moving longitudinally through staple cartridge (510). Due to the biasing of ribs (566) toward their unflexed states, once such a portion of the driving assembly has moved sufficiently distally to disengage a pair of ribs (566), the respective ribs (566) may return to their unflexed states to allow their laterally inner ends to resume confronting and/or contacting each other. In some versions, the laterally inner ends of ribs (566) may be tapered laterally outwardly in the proximal direction to define one or more cam surfaces (not shown) for assisting in the urging of ribs (566) distally by the driving assembly.

While six ribs (566) are shown in three laterally-opposed pairs, it will be appreciated that any suitable number of ribs (566) may be provided in any suitable arrangement. Moreover, deflectable cartridge support features may be provided in any other suitable configurations, as described in greater detail below.

D. Fourth Alternative Staple Cartridge with Truncated Circular Orifice

Figure 31:
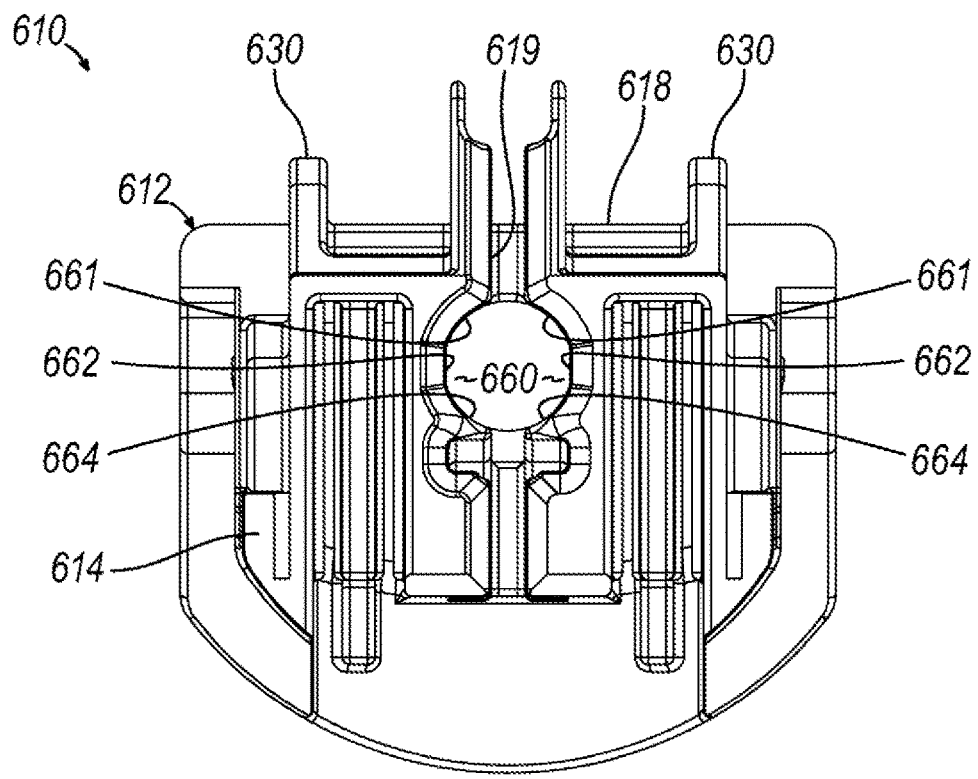
FIG. 31 depicts a rear elevation view of another exemplary staple cartridge having a truncated circle-shaped orifice for accommodating the push rod shown in FIG. 8 and/or the guide member shown in FIG. 9.

In some instances, it may be desirable to provide a staple cartridge configured for allowing the firing and/or guide member(s) to horizontally stabilize the cartridge body in a manner different from that described above in connection with FIGS. 29 and 30. FIG. 31 shows an exemplary staple cartridge (610) for use with either end effector (116, 210) described above that provides such functionalities. Staple cartridge (610) is similar to staple cartridge (510) described above except as otherwise described below. In this regard, staple cartridge (610) includes a staple cartridge body (612) having a proximal end (614) and an upper deck (618). A vertical slot (619) extends through part of staple cartridge (610), and a laterally-opposed pair of tissue stops (630) protrude upwardly from a proximal portion of upper deck (518).

In the example shown, a longitudinal orifice (660), configured to accommodate a firing member (not shown), such as push rod (168), and/or to accommodate a guide member of a wedge sled (not shown), such as guide member (190), extends laterally outwardly from both sides of vertical slot (619). Orifice (660) is defined by a laterally-opposed pair of upper arc-shaped surfaces (661) extending laterally outwardly and downwardly from upper portions of respective sides of vertical slot (619), a laterally-opposed pair of intermediate flat surfaces (662) extending downwardly from corresponding upper arc-shaped surfaces (661), and a laterally-opposed pair of lower arc-shaped surfaces (664) extending laterally outwardly and upwardly from lower portions of respective sides of vertical slot (619) to corresponding intermediate flat surfaces (662). In this manner, orifice (660) may have a generally truncated-circular cross section, bifurcated by and symmetrical relative to vertical slot (619). In some versions, arc-shaped surfaces (661, 664) of orifice (660) may be defined by a uniform radius, and each flat surface (562, 564) may be oriented generally parallel relative to vertical slot (619).

In some versions, the cross-sectional shape of orifice (660) may be substantially different from that of the firing and/or guide member(s) accommodated by orifice (660). For example, push rod (168) and guide member (190) described above each have generally round and/or circular cross-sectional shapes substantially different from the truncated circular cross-sectional shape of orifice (660). Moreover, such differently-shaped firing and/or guide member(s) may be sized to contact flat surfaces (662) of orifice (660) at predetermined locations therealong. For example, the rounded and/or circular cross-sectional shapes of push rod (168) and/or guide member (190) may be defined by at least one radius substantially equal to or slightly greater than the shortest distances between a centerpoint of orifice (660) and each of the flat surfaces (662). It will be appreciated that such shortest distances may occur at or near a midpoint of each of the flat surfaces (662). In this manner, the firing and/or guide member(s), such as push rod (168) and/or guide member (190), may contact each flat surface (662) at or near the midpoint thereof while moving longitudinally through staple cartridge (610) to thereby horizontally stabilize cartridge body (612). For example, push rod (168) and/or guide member (190) may inhibit laterally inward deflection (e.g., buckling) of cartridge body (612). In this regard, push rod (168) and/or guide member (190) may urge the corresponding portions of cartridge body (612) on either side of vertical slot (619) toward a substantially vertical orientation by counteracting any laterally-inwardly directed forces that might be applied to such portions of cartridge body (612) during use (e.g., clamping and/or firing).

E. Fifth Alternative Staple Cartridge with Cartridge Support Ribbon

Figure 32:
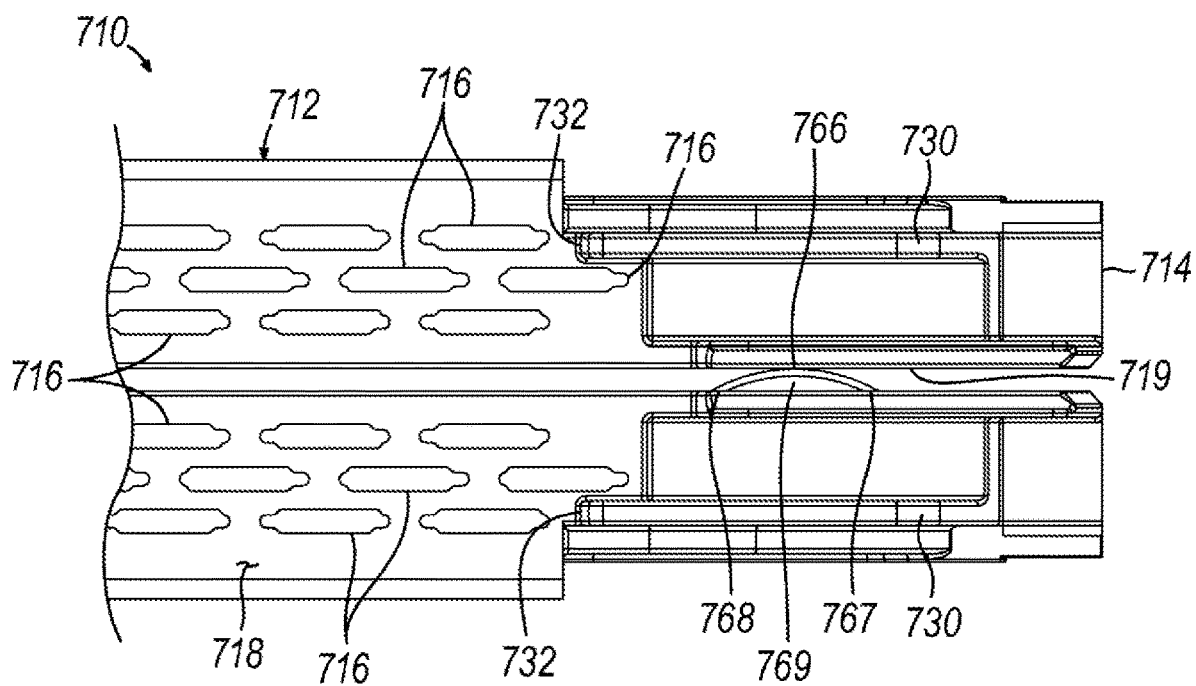
FIG. 32 depicts a partial top view of another exemplary staple cartridge having a cartridge support feature extending laterally inwardly from one side of a vertical slot of the staple cartridge toward an opposing side of the vertical slot.

In some instances, it may be desirable to provide a staple cartridge with a cartridge support feature different from those described above in connection with FIGS. 29 and 30. FIG. 32 shows an exemplary staple cartridge (710) for use with either end effector (116, 210) described above that provides such functionalities. Staple cartridge (710) is similar to staple cartridge (510) described above except as otherwise described below. In this regard, staple cartridge (710) includes a staple cartridge body (712) having a proximal end (714) and an array of staple apertures (716) extending through an upper deck (718). A vertical slot (719) extends through part of staple cartridge (710), and a laterally-opposed pair of tissue stops (730) protrude upwardly from a proximal portion of upper deck (718) and terminate distally at respective distal ends (732).

In the example shown, a deflectable cartridge support feature in the form of a longitudinal, flexible ribbon (766) extends laterally inwardly from one side of vertical slot (719). Ribbon (766) includes a proximal end (767) and a distal end (768), and is bowed laterally inwardly between proximal and distal ends (767, 768) to define a relief space (769). In some versions, ribbon (766) may be arranged in a proximal, upper portion of cartridge body (712), such as with ribbon (766) positioned above upper deck (718) and/or proximally of distal ends (732 of tissue stops (730).

In the present version, ribbon (766) is configured to flex (e.g., bend and/or fold) in the lateral direction (e.g., laterally outwardly) into relief space (769), and is resiliently biased in the lateral direction (e.g., laterally inwardly) to its unflexed state away from relief space (769), as shown in FIG. 32. For example, ribbon (766) may be constructed as a leaf spring. The bowed configuration of ribbon (766) relative to the adjoining portion of cartridge body (712) may assist in maintaining ribbon (766) in its unflexed state in the absence of longitudinally-directed external forces acting upon ribbon (766).

In the example shown, ribbon (766) bridges across vertical slot (719), such that a midsection of ribbon (766) confronts and is configured to contact the portion of cartridge body (712) on the opposite side of vertical slot (719) to thereby horizontally stabilize cartridge body (712). For example, ribbon (766) may inhibit laterally inward deflection (e.g., buckling) of cartridge body (712). In this regard, ribbon (766) may each urge the portions of cartridge body (712) on both sides of vertical slot (719) toward a substantially vertical orientation by counteracting any laterally-inwardly directed forces that might be applied to such portions of cartridge body (712) during use (e.g., clamping and/or firing). Due to the flexibility of ribbon (766) in the lateral direction, a portion of a driving assembly (not shown), such as pusher member (166) or vertical rib member (192) of wedge sled (170), may engage ribbon (766) and urge ribbon (766) laterally outwardly to its flexed state to thereby permit advancement of the driving assembly while moving longitudinally through staple cartridge (710). Due to the biasing of ribbon (766) toward its unflexed state, once such a portion of the driving assembly has moved sufficiently distally to disengage ribbon (766), ribbon (766) may return to its unflexed state to bridge across vertical slot (719) and allow the midsection of ribbon (766) to resume confronting and/or contacting the portion of cartridge body (712) on the opposite side of vertical slot (719). In some versions, the curvature of the outer, proximal surface of ribbon (766) resulting from its bowed configuration may assist in the urging of ribbon (766) laterally outwardly by the driving assembly.

F. Sixth Alternative Staple Cartridge with Driver Retention Detents

Figure 33:
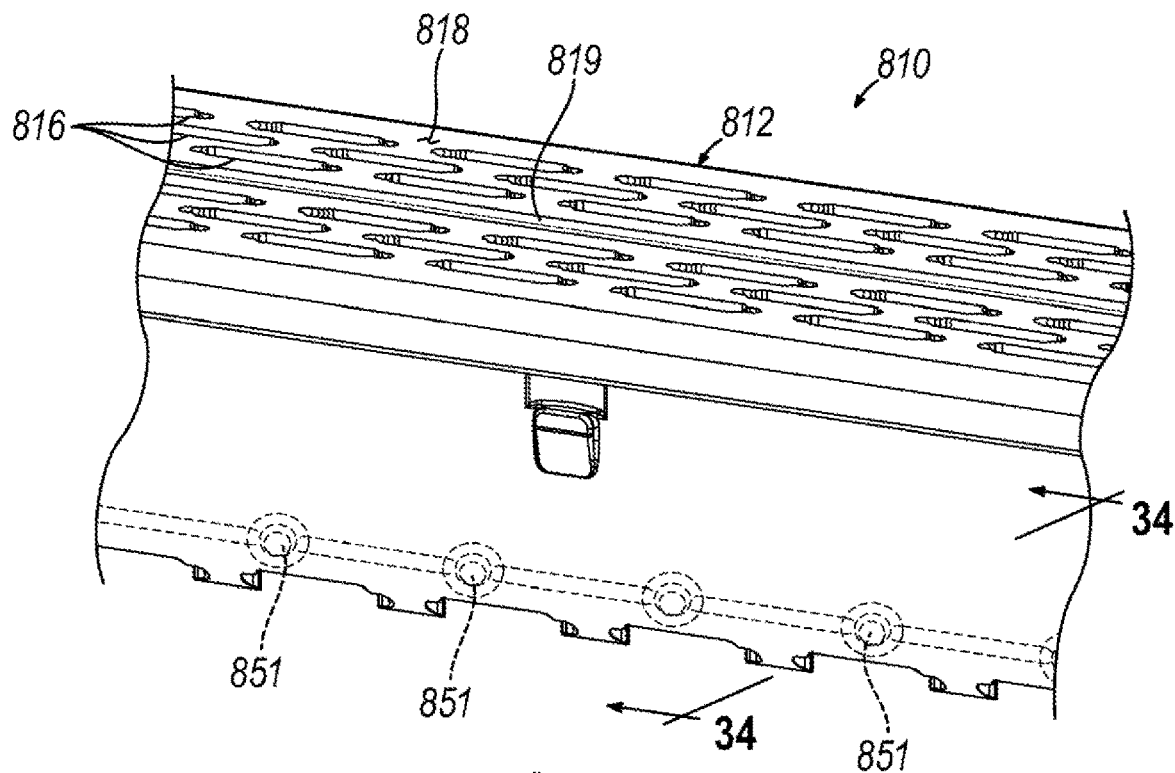
FIG. 33 depicts a partial perspective view of another exemplary staple cartridge having staple driver retention features.
Figure 34:
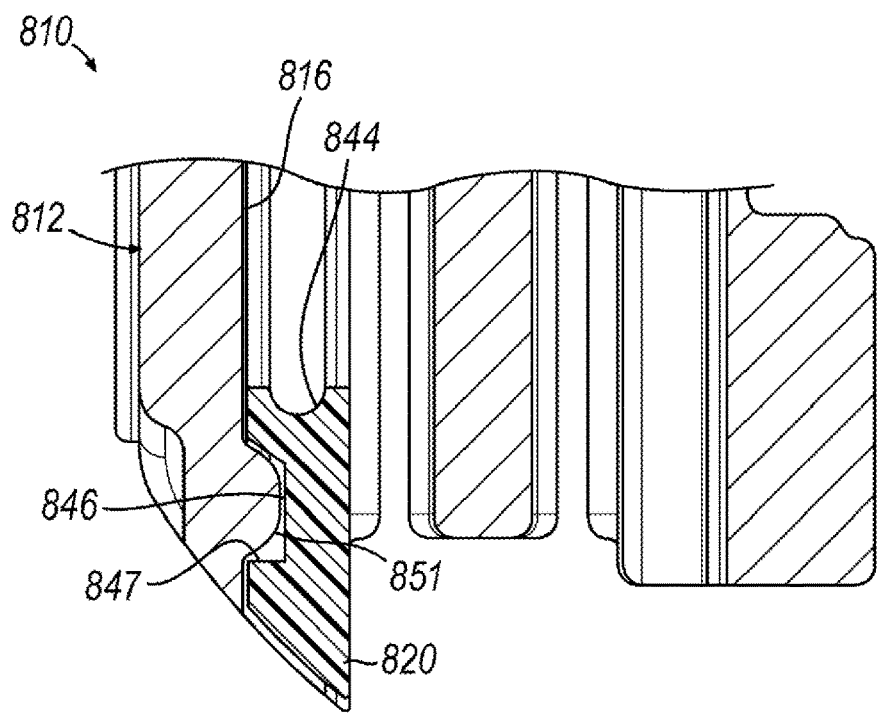
FIG. 34 depicts a cross-sectional view of the staple cartridge of FIG. 33, taken along section line 34-34 in FIG. 33, showing a staple driver retention feature engaging a staple driver of the staple cartridge.

In some instances, it may be desirable to provide a staple cartridge with staple driver retention features for assisting with maintaining staple drivers within the cartridge body prior to firing. FIGS. 33 and 34 show an exemplary staple cartridge (810) for use with either end effector (116, 210) described above that provides such functionalities. Staple cartridge (810) is similar to staple cartridge (310) described above except as otherwise described below. In this regard, staple cartridge (810) includes a staple cartridge body (812) having an array of staple apertures (816) extending through an upper deck (818). A vertical slot (819) extends through part of staple cartridge (810). Staple cartridge body (812) is also configured to house a plurality of staple drivers (820) (FIG. 34), and to house a plurality of staples (not shown), such as staples (162, 250).

As shown in FIG. 34, each staple driver (820) includes at least one longitudinal groove (844) configured to cradle a crown (not shown) of a corresponding one of staples (162, 250), and presents an inclined cam surface (not shown) configured to be cammingly contacted by a respective ramp portion (182) (FIG. 9) of wedge sled (170). In the present version, each staple driver (820) further includes a driver retention recess (846) extending laterally inwardly from a laterally outer surface of the staple driver (820) to define a lower ledge (847).

As best shown in FIG. 34, staple cartridge body (812) also includes a plurality of driver retention detents (851) (one shown) protruding laterally inwardly from a laterally inner side of staple cartridge body (812) and aligned in the lateral direction with respective driver retention recesses (846). In this manner, each driver retention detent (851) may be at least partially received within the respective driver retention recess (846) such that each driver retention detent (851) may be configured to abut the lower ledge (847) of the respective driver retention recess (846) for inhibiting upward movement of each staple driver (820) relative to staple cartridge body (812). In some versions, driver retention detents (851) may each be deflectable in the lateral direction (e.g., laterally outwardly) upon application of a threshold force thereto for disengaging the respective driver retention recess (846). For example, driver retention detents (851) may be deformable and biased toward their respective illustrated undeformed states, such that driver retention detents (851) may each be capable of being deformed laterally outwardly from their respective undeformed states to their respective deformed states (not shown). In such cases, driver retention detents (851) may be referred to as "crush bumps."

In any event, the threshold force for deflecting driver retention detents (851) for disengaging the respective driver retention recess (846) may be selected to be greater than any incidental forces that might be applied to a driver retention detent (851) by the lower ledge (847) of the respective driver retention recess (846) during transit, loading, and/or general handling of staple cartridge (810), and to be less than or equal to the force applied to each driver retention detent (851) by the lower ledge (847) of the respective driver retention recess (846) when wedge sled (170) is driven distally into upward camming contact with staple drivers (820) during firing. Thus, the interaction between lower ledges (847) of driver retention recesses (846) and driver retention detents (851) may inhibit inadvertent dislodgement of staple drivers (820) without interfering with deployment of staples (162, 250) during firing. In some versions, driver retention detents (851) may be formed via heat staking. In addition or alternatively, lower ledges (847) may be tapered laterally outwardly in the downward direction to define one or more cam surfaces (not shown) for assisting in the deflection of driver retention detents (851) laterally outwardly during firing.

G. Seventh Alternative Staple Cartridge with Driver Retention Tabs

Figure 35A:
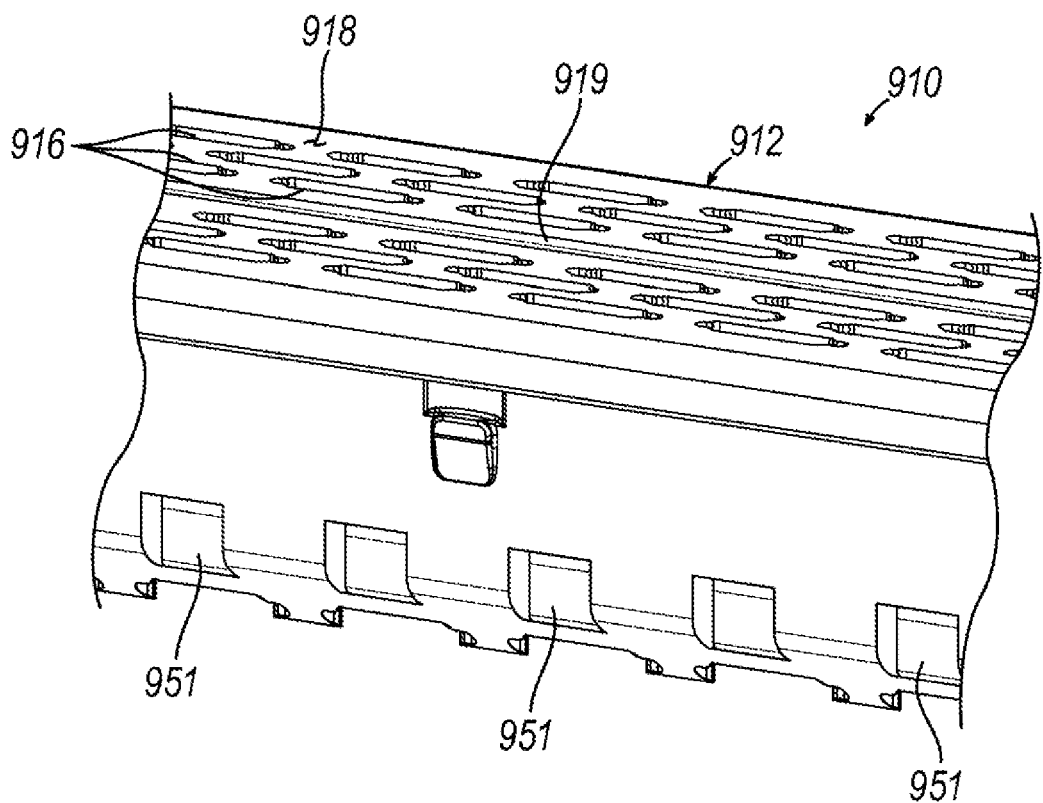
FIG. 35A depicts a partial perspective view of another exemplary staple cartridge having staple driver retention features, showing the staple driver retention features in respective undeformed states.
Figure 35B:
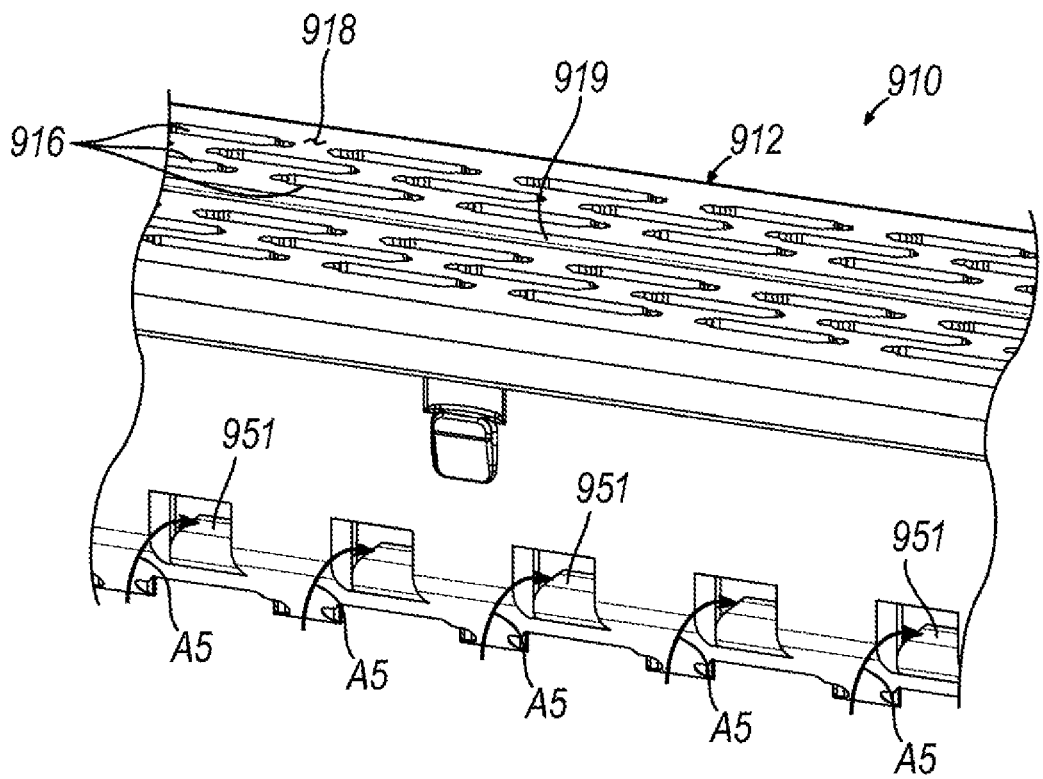
FIG. 35B depicts a partial perspective view of the staple cartridge of FIG. 35A, showing the staple driver retention features in respective deformed states for engaging respective staple drivers.

In some instances, it may be desirable to provide a staple cartridge with staple driver retention features different from those described above in connection with FIGS. 33 and 34. FIGS. 35A and 35B show an exemplary staple cartridge (910) for use with either end effector (116, 210) described above that provides such functionalities. Staple cartridge (910) is similar to staple cartridge (810) described above except as otherwise described below. In this regard, staple cartridge (910) includes a staple cartridge body (912) having an array of staple apertures (916) extending through an upper deck (918). A vertical slot (919) extends through part of staple cartridge (910). Staple cartridge body (912) is also configured to house a plurality of staple drivers (not shown), such as staple drivers (820), and to house a plurality of staples (not shown), such as staples (162, 250).

As shown, staple cartridge body (912) also includes a plurality of driver retention tabs (951) bending laterally inwardly from a laterally outer side of staple cartridge body (912) and which may be aligned in the lateral direction with respective driver retention recesses (846). In this manner, each driver retention tab (951) may be at least partially received within the respective driver retention recess (846) such that each driver retention tab (951) may be configured to abut the lower ledge (847) of the respective driver retention recess (846) for inhibiting upward movement of each staple driver (820) relative to staple cartridge body (912). In some versions, driver retention tabs (951) may each be deflectable in the lateral direction (e.g., laterally outwardly) upon application of a threshold force thereto. For example, driver retention detents (851) may be initially bent from respective undeformed states (FIG. 35A) to respective deformed states (FIG. 35B) for receipt within the respective driver retention recesses (846), as indicated by arrows (A5) in FIG. 35B, such that driver retention tabs (951) may each be capable of being subsequently deflected from their respective deformed states to their respective undeformed states upon application of a threshold force thereto for disengaging the respective driver retention recess (846).

In any event, the threshold force for deflecting driver retention tabs (951) for disengaging the respective driver retention recess (846) may be selected to be greater than any incidental forces that might be applied to a driver retention tab (951) by the lower ledge (847) of the respective driver retention recess (846) during transit, loading, and/or general handling of staple cartridge (910), and to be less than or equal to the force applied to each driver retention tab (951) by the lower ledge (847) of the respective driver retention recess (846) when wedge sled (170) is driven distally into upward camming contact with staple drivers (820) during firing. Thus, the interaction between lower ledges (847) of driver retention recesses (846) and driver retention tabs (951) may inhibit inadvertent dislodgement of staple drivers (820) without interfering with deployment of staples (162, 250) during firing. In some versions, driver retention tabs (951) may be formed via molding together with the remainder of staple cartridge body (912).

H. Alternative Cartridge Tray with Support Tabs

Figure 36:
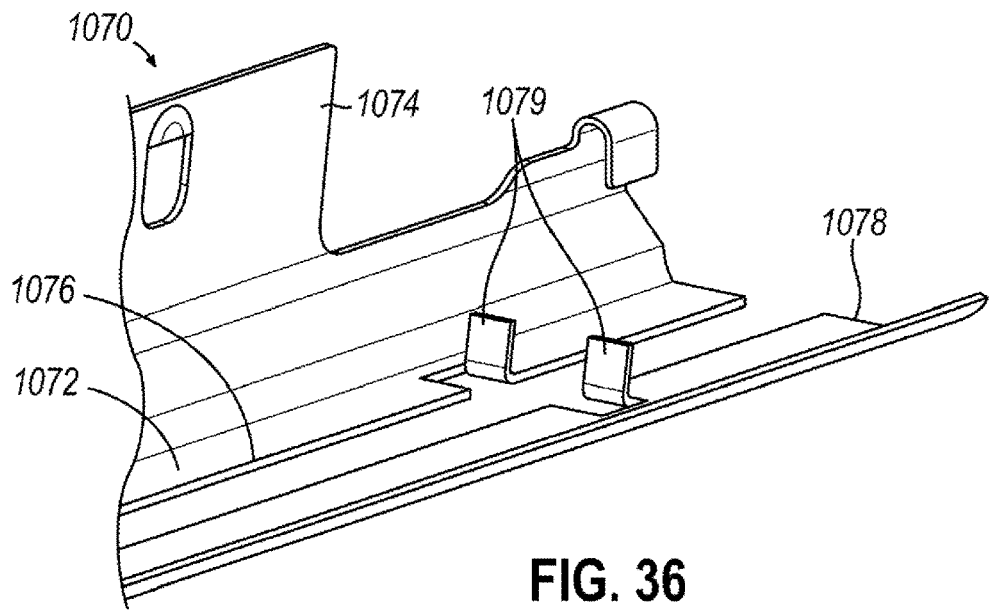
FIG. 36 depicts a partial perspective view of an exemplary cartridge tray having cartridge support features.

In some instances, it may be desirable to provide a cartridge tray that is configured to provide rigidity to any one or more of staple cartridges (154, 218, 310, 410, 510, 610, 710, 810, 910) by supporting and/or stabilizing the sides of the respective staple cartridge body (156, 220, 312, 412, 512, 612, 712, 812, 912) above the cartridge tray. FIGS. 36-37B show an exemplary cartridge tray (1070) for use with either end effector (116, 210) described above that provides such functionalities. Cartridge tray (1070) is similar to cartridge tray (224) described above except as otherwise described below, and is configured to snap-fit, clip, or otherwise couple to a lower portion of any one or more of cartridge bodies (156, 220, 312, 412, 512, 612, 712, 812, 912). In some examples, cartridge tray (1070) comprises a metallic material to provide added structural rigidity to the respective staple cartridge (154, 218, 310, 410, 510, 610, 710, 810, 910).

Cartridge tray (1070) of the present example includes a floor (1072) and a pair of sidewalls (1074) extending from a proximal end (1078) of cartridge tray (1070). A longitudinal slot (1076) is defined by floor (1072) extending from proximal end (1078) of cartridge tray (1070). Longitudinal slot (1076) is generally configured to permit a portion of an actuation assembly, also referred to as driving assembly (164) to pass through cartridge tray (1070) for engagement of second flange (185) with longitudinal slot (187) of lower jaw (152).

Cartridge tray (1070) further includes a pair of cartridge support tabs (1079) extending upwardly from floor (1072). The particular extension of each support tab (1079) in the present example is generally about perpendicular to a longitudinal axis defined by floor (1072), although other angles of extension relative to floor (1072) may be used in other examples. Each support tab (1079) is positioned proximate proximal end (1078) of cartridge tray (1070). It will be appreciated that support tabs (1079) may be positioned at any other suitable location(s) along the length of cartridge tray (1070).

The construction of each support tab (1079) of the present example is integral with floor (1072) and positioned on opposite sides of longitudinal slot (1076). Specifically, each support tab (1079) is defined by a cutout portion of floor (1072) that is bent upwardly or perpendicularly relative to the extension of floor (1072). Thus, each support tab (1079) in the present example is generally of the same material of floor (1072). The particular material used may be metal or other similarly rigid materials. Although an integral construction is used in the present example for support tab (1079), it should be understood that in other examples each support tab (1079) may be an independent component from floor (1072) and coupled thereto.

Each support tab (1079) in the present example is configured to have at least some rigidity. As will be described in greater detail below, such rigidity may permit each support tab (1079) to vertically support a cartridge body (156, 220, 312, 412, 512, 612, 712, 812, 912) coupled to cartridge tray (1070). Additionally, such rigidity may also be configured in some examples to provide additional structural rigidity to cartridge tray (1070), particularly at the interface between floor (1072) and each support tab (1079). In some examples, such rigidity may permit each support tab (1079) to hold wedge sled (170) in a predetermined position. Examples of suitable cartridge trays (1070) having retention characteristics are described in U.S. patent application Ser. No. 17/403,732, entitled "Multi-Position Restraining Member for Sled Movement," filed on Aug. 16, 2021, issued as U.S. Pat. No. 11,986,182 on May 21, 2024, the disclosure of which is hereby incorporated by reference herein in its entirety.

Each support tab (1079) in the present example is also configured to have at least some flexibility. As will also be described in greater detail below, such flexibility may permit each support tab (1079) to move in response to movement of wedge sled (170) driven by pusher member (166). Each support tab (1079) may also have a resilient characteristic such that each support tab (1079) may be resiliently biased toward the upwardly extended position shown in FIGS. 36 and 37A.

Figure 37A:
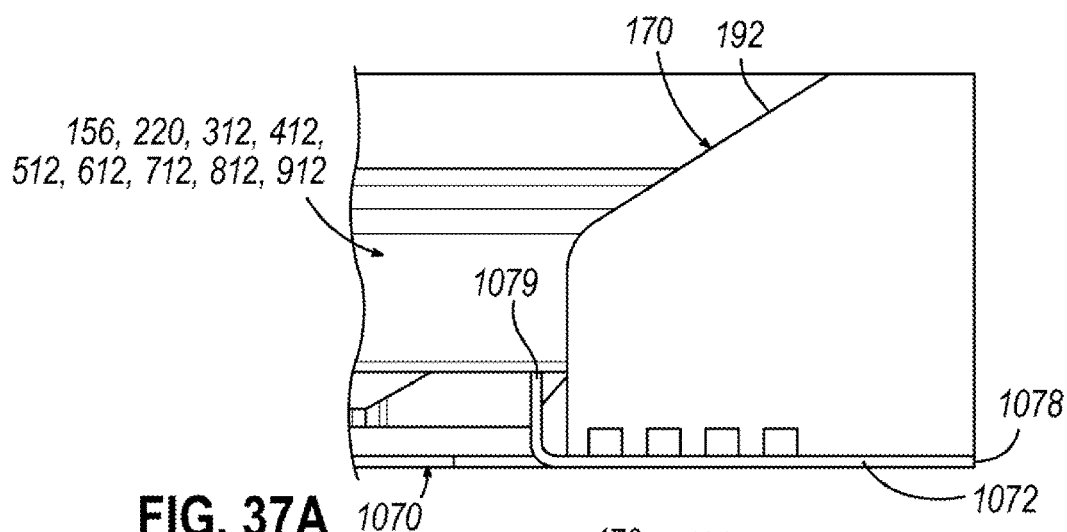
FIG. 37A depicts a side elevation view of the cartridge tray of FIG. 36, showing the wedge sled of FIG. 9 in a proximal position relative to the cartridge support features, and further showing the cartridge support features in vertical orientations.
Figure 37B:
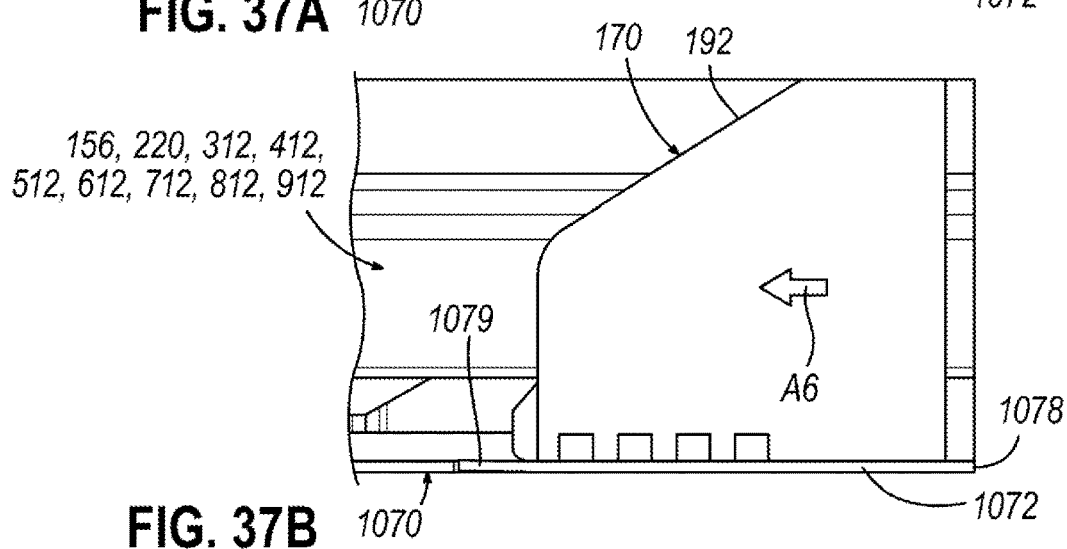
FIG. 37B depicts a side elevation view of the cartridge tray of FIG. 36, showing the cartridge support features flattened toward horizontal orientations by the wedge sled of FIG. 9 during distal translation of the wedge sled.

FIGS. 37A and 37B show an exemplary use of support tabs (1079) in connection with wedge sled (170). As can be seen, wedge sled (170) begins proximate proximal end (1078) of cartridge tray (1070). This position of wedge sled (170) may also correspond to wedge sled (170) being proximate the proximal end of the respective staple cartridge (154, 218, 310, 410, 510, 610, 710, 810, 910). In this position, the upper ends of support tabs (1079) are configured to contact the portions of the respective cartridge body (156, 220, 312, 412, 512, 612, 712, 812, 912) on the corresponding sides of longitudinal slot (1076) and thereby provide vertical support to cartridge body (156, 220, 312, 412, 512, 612, 712, 812, 912).

As described above, wedge sled (170) may be driven distally within cartridge body (156, 220, 312, 412, 512, 612, 712, 812, 912) to drive staples using wedge sled (170) and sever tissue using cutting edge (194) of knife member (172), as indicated by arrow (A6) in FIG. 37B. As seen in FIG. 37B, once wedge sled (170) is driven by pusher member (166), the force supplied by pusher member (166) may be sufficient to overcome the rigidity of each support tab (1079). This causes each support tab (1079) to move and/or pivot away from wedge sled (170) from the upward orientation described above to a horizontal position about parallel to the extension of floor (1072).

Once each support tab (1079) is pushed to the horizontal position, wedge sled (170) may be driven distally by pusher member (166) to drive staples and sever tissue. In the present example, each support tab (1079) is generally configured to resiliently bend in response to wedge sled (170) being driven by pusher member (166). Thus, each support tab (1079) may return to the upwardly extended position after wedge sled (170) has been driven distally past each support tab (1079) to resume vertically supporting cartridge body (156, 220, 312, 412, 512, 612, 712, 812, 912).

I. Alternative Wedge Sled with Elongate Nose

Figure 38:
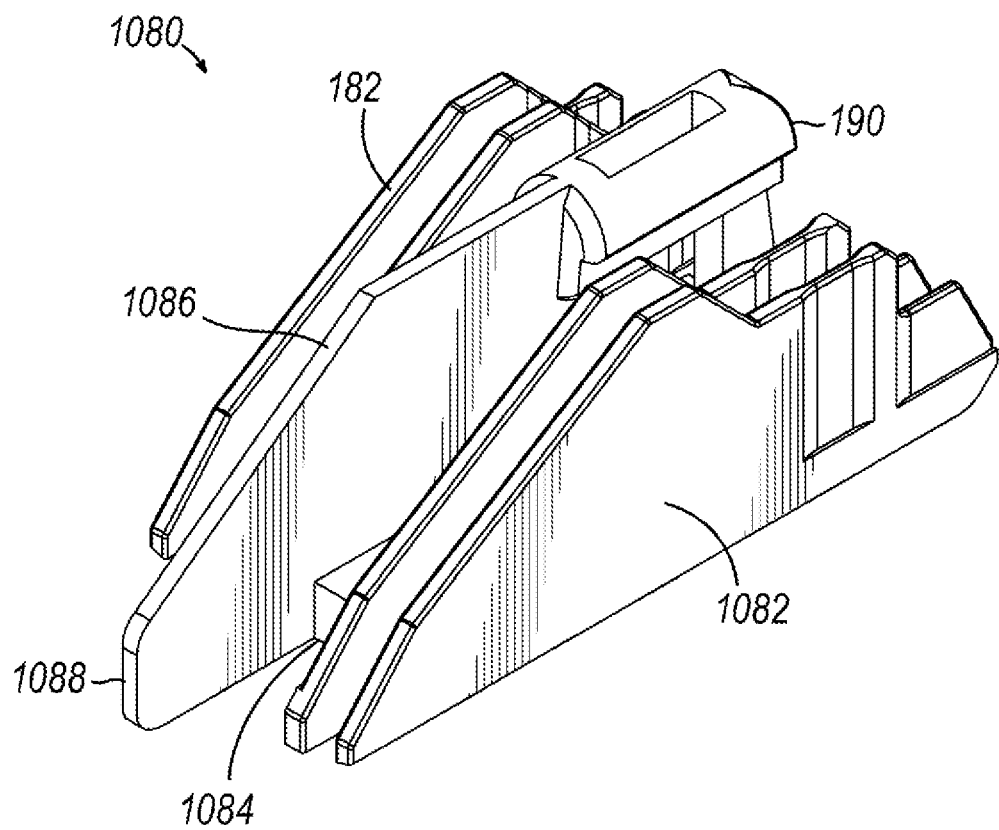
FIG. 38 depicts a perspective view of another exemplary wedge sled having an elongate distal nose.

In some instances, it may be desirable to provide a wedge sled that is configured to provide rigidity to any one or more of staple cartridges (154, 218, 310, 410, 510, 610, 710, 810, 910) by supporting and/or stabilizing the sides of the respective staple cartridge body (156, 220, 312, 412, 512, 612, 712, 812, 912) adjacent to the wedge sled. FIG. 38 shows an exemplary staple actuator in the form of a wedge sled (1080) for use with either end effector (116, 210) described above that provides such functionalities. Wedge sled (1080) is similar to wedge sled (170) described above except as otherwise described below. In this regard, wedge sled (1080)

includes ramp portions (182) and guide member (190), and is configured to advance distally along a staple cartridge body (not shown), such as any one or more of staple cartridge bodies (156, 220, 312, 412, 512, 612, 712, 812, 912) such that ramp portions (182) cammingly contact staple drivers (not shown) housed therein.

In the example shown, ramp portions (182) are presented by respective rails (1082) extending upwardly from a base platform (1084). In the example shown, rails (1082) each terminate distally at respective distal rail ends that are distal relative to a distal end of base platform (1084). One or more rails (1082) may terminate proximally at respective proximal rail ends that are proximal relative to a proximal end of base platform (1084). In some versions, such proximal rail ends may be proximal relative to the proximal end of cartridge body (156, 220, 312, 412, 512, 612, 712, 812, 912) when wedge sled (1080) is at its initial proximal position. Such proximal elongation of rails (1082) relative to base platform (1084) may assist with maintaining alignment of wedge sled (1080) with staple cartridge body (156, 220, 312, 412, 512, 612, 712, 812, 912) during firing. In this regard, at least the proximal portions of rails (1082) may be configured to slidably contact or otherwise engage respective internal side surfaces of cartridge body (156, 220, 312, 412, 512, 612, 712, 812, 912) while wedge sled (1080) moves longitudinally through the respective staple cartridge (154, 218, 310, 410, 510, 610, 710, 810, 910) to maintain alignment of wedge sled (1080) with cartridge body (156, 220, 312, 412, 512, 612, 712, 812, 912) in the lateral direction. Such engagement may also horizontally stabilize the cartridge body (156, 220, 312, 412, 512, 612, 712, 812, 912). For example, at least the proximal portions of rails (1082) may inhibit laterally inward and/or laterally outward deflection (e.g., bending) of cartridge body (156, 220, 312, 412, 512, 612, 712, 812, 912).

In the example shown, guide member (190) extends from a central nose (1086) of wedge sled (1080). Central nose (1086) extends upwardly from base platform (1084) between the laterally inner rails (1082) and also extends distally from base platform (1084) to a distal tip (1088). Such distal elongation of central nose (1086) relative to base platform (1084) may assist with maintaining alignment of wedge sled (1080) with a staple cartridge body (not shown), such as any one or more of staple cartridge bodies (156, 220, 312, 412, 512, 612, 712, 812, 912), during firing. In this regard, at least the distal portion of central nose (1086) may be configured to slidably contact or otherwise engage both sides of the vertical slot of cartridge body (156, 220, 312, 412, 512, 612, 712, 812, 912) while wedge sled (1080) moves longitudinally through the respective staple cartridge (154, 218, 310, 410, 510, 610, 710, 810, 910) to maintain alignment of wedge sled (1080) with cartridge body (156, 220, 312, 412, 512, 612, 712, 812, 912) in the lateral direction. Such engagement may also horizontally stabilize the cartridge body (156, 220, 312, 412, 512, 612, 712, 812, 912). For example, at least the distal portion of central nose (1086) may inhibit laterally inward and/or laterally outward deflection (e.g., bending) of cartridge body (156, 220, 312, 412, 512, 612, 712, 812, 912). In some versions, the distal elongation of central nose (1086) relative to base platform (1084) may also assist with inhibiting inadvertent rolling of wedge sled (1080) during firing.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument comprising: (a) a shaft assembly extending along a longitudinal axis to a distal end; (b) an end effector at the distal end of the shaft assembly, wherein the end effector includes: (i) a first jaw having an anvil, and (ii) a second jaw, wherein the first and second jaws are operable to clamp tissue therebetween; and (c) a stapling assembly supported by the second jaw of the end effector, wherein the stapling assembly includes: (i) a plurality of staples, (ii) a staple actuator translatable distally through the stapling assembly along the longitudinal axis, and (iii) a first driver assembly, wherein the first driver assembly includes: (A) a laterally-opposed pair of distal drivers that receive respective staples of the plurality of staples, (B) a proximal driver that receives a respective staple of the plurality of staples, and (C) a cam surface, wherein the staple actuator is configured to engage the cam surface of the first driver assembly during distal translation of the staple actuator to drive the respective staples into contact with the anvil of the first jaw, wherein the staple actuator and the cam surface are configured such that, when the respective staples contact the anvil of the first jaw, the engagement between the staple actuator and the cam surface of the first driver assembly is centered at a location along the cam surface distal of a centroid of the first driver assembly.

Example 2

The surgical stapling instrument of Example 1, wherein the first driver assembly further includes at least one rigger extending between the proximal driver and at least one of the distal drivers, wherein the cam surface is presented by the at least one rigger.

Example 3

The surgical stapling instrument of any one or more of Examples 1 through 2, wherein the cam surface extends between a proximal cam surface end and a distal cam surface end, wherein the cam surface is inclined downwardly toward the distal cam surface end, wherein the distal cam surface end is substantially distal of the centroid.

Example 4

The surgical stapling instrument of any one or more of Example 3, wherein the cam surface includes a midpoint between the proximal and distal cam surface ends, wherein the midpoint is substantially distal of the centroid.

Example 5

The surgical stapling instrument of any one or more of Examples 1 through 4, wherein the location is positioned below the centroid and spaced apart therefrom by a vertical distance, wherein the cam surface is oriented at an angle relative to a horizontal reference plane, wherein the vertical distance and the angle have a ratio of between approximately 0.025:25 and approximately 0.1:15.

Example 6

The surgical stapling instrument of Example 5, wherein the vertical distance is between approximately 0.025 inch and approximately 0.1 inch, wherein the angle is between approximately 15° and approximately 25°.

Example 7

The surgical stapling instrument of any one or more of Examples 1 through 6, wherein the stapling assembly further includes: (a) a deck; (b) a laterally-opposed pair of tissue stops protruding upwardly from the deck, wherein each tissue stop includes a proximal tissue stop end and a distal tissue stop end; and (c) a plurality of staple apertures extending through the deck, wherein each staple aperture includes a proximal staple aperture end and a distal staple aperture end, wherein at least one of the distal staple aperture ends is proximal of at least one of the distal tissue stop ends.

Example 8

The surgical stapling instrument of any one or more of Examples 1 through 7, wherein the stapling assembly further includes a second driver assembly, wherein the second driver assembly includes: (a) a laterally-opposed pair of distal drivers receiving respective staples of the plurality of staples; (b) a proximal driver receiving a respective staple of the plurality of staples; (c) an intermediate driver receiving a respective staple of the plurality of staples; (d) a proximal cam surface; and (e) a distal cam surface oriented at an oblique angle relative to the proximal cam surface.

Example 9

The surgical stapling instrument of Example 8, wherein the second driver assembly further includes at least one rigger extending between the intermediate driver and at least one of the distal or proximal drivers of the second driver assembly.

Example 10

The surgical stapling instrument of Example 9, wherein the proximal and distal cam surfaces are each presented by the at least one rigger of the second driver assembly.

Example 11

The surgical stapling instrument of any one or more of Examples 1 through 10, further comprising a push rod configured to translate the staple actuator distally through the stapling assembly along the longitudinal axis, wherein the stapling assembly further includes an elongate orifice extending longitudinally for receiving the push rod, wherein the orifice is defined by at least one flat surface.

Example 12

The surgical stapling instrument of any one or more of Examples 1 through 11, wherein the stapling assembly further includes: (a) an elongate slot extending longitudinally for receiving a portion of the staple actuator; and (b) at least one stapling assembly support member extending laterally inwardly from one side of the elongate slot toward an opposing side of the elongate slot, wherein the at least one stapling assembly support member is configured to be deflected laterally outwardly by the portion of the staple actuator during distal translation of the staple actuator.

Example 13

The surgical stapling instrument of any one or more of Examples 1 through 12, wherein the stapling assembly further includes at least one driver retention member extending laterally inwardly to engage a portion of the first driver assembly, wherein the at least one driver retention member is configured to be deflected laterally outwardly by the portion of the first driver assembly during distal translation of the staple actuator.

Example 14

The surgical stapling instrument of any one or more of Examples 1 through 13, wherein the stapling assembly further includes a cartridge comprising: (a) a cartridge body; and (b) a cartridge tray, wherein the staple actuator is captured between the cartridge body and the cartridge tray, wherein the cartridge tray includes at least one cartridge support member extending upwardly to engage a portion of the cartridge body, wherein the at least one cartridge support member is configured to be deflected downwardly by a portion of the staple actuator during distal translation of the staple actuator.

Example 15

The surgical stapling instrument of any one or more of Examples 1 through 14, wherein the staple actuator includes: (a) a base platform; (b) a plurality of rails protruding upwardly from the base platform; and (c) a central nose protruding upwardly and distally from the base platform.

Example 16

A stapling assembly for a surgical stapling instrument, comprising: (a) a plurality of staples; (b) a staple actuator translatable distally through the stapling assembly along a longitudinal axis; and (c) a driver assembly, wherein the driver assembly includes: (i) a laterally-opposed pair of distal drivers that receive respective staples of the plurality of staples, (ii) a proximal driver that receives a respective staple of the plurality of staples, and (iii) a cam surface, wherein the staple actuator is configured to engage the cam surface of the driver assembly during distal translation of the staple actuator to drive the respective staples upwardly, wherein the staple actuator and the cam surface are configured such that, when the respective staples are driven between 0.05 inch and 0.065 inch upwardly from a starting position, the engagement between the staple actuator and the cam surface of the first driver assembly is centered at a location along the cam surface distal of a centroid of the first driver assembly.

Example 17

The stapling assembly of Example 16, wherein the cam surface extends between a proximal cam surface end and a distal cam surface end, wherein the cam surface is inclined downwardly toward the distal cam surface end, wherein the distal cam surface end is substantially distal of the centroid.

Example 18

The stapling assembly of Example 17, wherein the cam surface includes a midpoint between the proximal and distal cam surface ends, wherein the midpoint is substantially distal of the centroid.

Example 19

The stapling assembly of Example 18, wherein the driver assembly further includes at least one rigger extending between the proximal driver and at least one of the distal drivers, wherein the cam surface is presented by the at least one rigger.

Example 20

A method of operating an apparatus comprising (i) an end effector having an anvil and a jaw, and (ii) a stapling assembly supported by the jaw and having a staple actuator and a driver assembly having (A) a laterally-opposed pair of distal drivers that receive respective staples, (B) a proximal driver that receives a respective staple, and (C) a cam surface, the method comprising: (a) translating the staple actuator distally through the stapling assembly along the longitudinal axis; (b) engaging the staple actuator with the cam surface of the driver assembly to drive the respective staples into contact with the anvil; (c) applying downward forces to distal ends of the distal drivers via the contact between the anvil and the respective staples; and (d) simultaneously with the act of applying downward forces, applying an upward, distal force to the cam surface of the driver assembly via the staple actuator at a location along the cam surface distal of a centroid of the driver assembly.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/088,941, entitled "Surgical Stapler End Effector Sled Having Cartridge Wall Support Feature," filed Nov. 4, 2020, issued as U.S. Pat. No. 11,540,826 on Jan. 3, 2023, the disclosure of which is hereby incorporated by reference herein in its entirety.

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, issued as U.S. Pat. No. 12,102,321 on Oct. 1, 2024; U.S. patent application Ser. No. 17/402,675, entitled "Multi-Threshold Motor Control Algorithm for Powered Surgical Stapler," filed on Aug. 16, 2021, issued as U.S. Pat. No. 11,992,209 on May 28, 2024; U.S. patent application Ser. No. 17/402,677, entitled "Variable Response Motor Control Algorithm for Powered Surgical Stapler," filed on Aug. 16, 2021, issued as U.S. Pat. No. 11,944,297 on Apr. 2, 2024; U.S. patent application Ser. No. 17/402,679, entitled "Powered Surgical Stapler Having Independently Operable Closure and Firing Systems," filed on Aug. 16, 2021, issued as U.S. Pat. No. 11,779,332 on Oct. 10, 2023; U.S. patent application Ser. No. 17/402,701, entitled "Multiple-Sensor Firing Lockout Mechanism for Powered Surgical Stapler," filed on Aug. 16, 2021, issued as U.S. Pat. No. 11,992,210 on May 28, 2024; U.S. patent application Ser. No. 17/402,703, entitled "Proximally Located Firing Lockout Mechanism for Surgical Stapler," filed on Aug. 16, 2021, issued as U.S. Pat. No. 11,957,336 on Apr. 16, 2024; U.S. patent application Ser. No. 17/402,720, entitled "Cartridge-Based Firing Lockout Mechanism for Surgical Stapler," filed on Aug. 16, 2021, issued as U.S. Pat. No. 12,011,164 on Jan. 18, 2024; U.S. patent application Ser. No. 17/402,732, entitled "Multi-Position Retraining Member for Sled Movement," filed on Aug. 16, 2021issued as U.S. Pat. No. 11,986,182 on May 21, 2024; U.S. patent application Ser. No. 17/402,738, entitled "Firing Member Tracking Feature for Surgical Stapler," filed on Aug. 16, 2021, issued as U.S. Pat. No. 12,171,428 on Dec. 24, 2024; U.S. patent application Ser. No. 17/402,744, entitled "Adjustable Power Transmission Mechanism for Powered Surgical Stapler," filed on Aug. 16, 2021, issued as U.S. Pat. No. 12,029,508 on Jul. 9, 2024; U.S. patent application Ser. No. 17/402,749, entitled "Firing Bailout System for Powered Surgical Stapler," filed on Aug. 16, 2021, issued as U.S. Pat. No. 12,089,842 on Sep. 17, 2024; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument comprising:
   (a) a shaft extending along a longitudinal axis to a distal end;
   (b) an end effector operatively coupled with the shaft, wherein the end effector includes:
      (i) a first jaw having an anvil, and
      (ii) a second jaw, wherein the first and second jaws are operable to clamp tissue therebetween; and
   (c) a stapling assembly supported by the second jaw of the end effector, wherein the stapling assembly includes:
      (i) a plurality of staples,
      (ii) a staple actuator translatable distally through the stapling assembly along the longitudinal axis, and
      (iii) a first driver assembly, wherein the first driver assembly includes:
         (A) a laterally-opposed pair of distal drivers that receive respective staples of the plurality of staples,
         (B) a proximal driver that receives a respective staple of the plurality of staples, and
         (C) a cam surface,
      wherein the staple actuator is configured to engage the cam surface of the first driver assembly during distal translation of the staple actuator to drive the respective staples into contact with the anvil of the first jaw, wherein the staple actuator and the cam surface are configured such that, when the respective staples contact the anvil of the first jaw, the engagement between the staple actuator and the cam surface of the first driver assembly is centered at a location along the cam surface distal of a centroid of the first driver assembly,
      wherein the location is positioned below the centroid and spaced apart therefrom by a vertical distance, wherein the cam surface is oriented at an angle relative to a horizontal reference plane, wherein the vertical distance and the angle have a ratio of between approximately 0.025:25 and approximately 0.1:15.

2. The surgical stapling instrument of claim 1, wherein the first driver assembly further includes at least one rigger extending between the proximal driver and at least one of the distal drivers, wherein the cam surface is presented by the at least one rigger.

3. The surgical stapling instrument of claim 1, wherein the cam surface extends between a proximal cam surface end and a distal cam surface end, wherein the cam surface is inclined downwardly toward the distal cam surface end, wherein the distal cam surface end is substantially distal of the centroid.

4. The surgical stapling instrument of claim 3, wherein the cam surface includes a midpoint between the proximal and distal cam surface ends, wherein the midpoint is substantially distal of the centroid.

5. The surgical stapling instrument of claim 1, wherein the vertical distance is between approximately 0.025 inch and approximately 0.1 inch, wherein the angle is between approximately 15° and approximately 25°.

6. The surgical stapling instrument of claim 1, wherein the stapling assembly further includes:
   (a) a deck;
   (b) a laterally-opposed pair of tissue stops protruding upwardly from the deck, wherein each tissue stop includes a proximal tissue stop end and a distal tissue stop end; and
   (c) a plurality of staple apertures extending through the deck, wherein each staple aperture includes a proximal staple aperture end and a distal staple aperture end,
   wherein at least one of the distal staple aperture ends is proximal of at least one of the distal tissue stop ends.

7. The surgical stapling instrument of claim 1, wherein the stapling assembly further includes a second driver assembly, wherein the second driver assembly includes:
   (a) a laterally-opposed pair of distal drivers receiving respective staples of the plurality of staples;
   (b) a proximal driver receiving a respective staple of the plurality of staples;
   (c) an intermediate driver receiving a respective staple of the plurality of staples;
   (d) a proximal cam surface; and
   (e) a distal cam surface oriented at an oblique angle relative to the proximal cam surface.

8. The surgical stapling instrument of claim 7, wherein the second driver assembly further includes at least one rigger extending between the intermediate driver and at least one of the distal or proximal drivers of the second driver assembly.

9. The surgical stapling instrument of claim 8, wherein the proximal and distal cam surfaces are each presented by the at least one rigger of the second driver assembly.

10. The surgical stapling instrument of claim 1, further comprising a push rod configured to translate the staple actuator distally through the stapling assembly along the longitudinal axis, wherein the stapling assembly further includes an elongate orifice extending longitudinally for receiving the push rod, wherein the orifice is defined by at least one flat surface.

11. A surgical stapling instrument comprising:
(a) a shaft extending along a longitudinal axis to a distal end;
(b) an end effector operatively coupled with the shaft, wherein the end effector includes:
   (i) a first jaw having an anvil, and
   (ii) a second jaw, wherein the first and second jaws are operable to clamp tissue therebetween; and
(c) a stapling assembly supported by the second jaw of the end effector, wherein the stapling assembly includes:
   (i) a plurality of staples,
   (ii) a staple actuator translatable distally through the stapling assembly along the longitudinal axis, and
   (iii) a first driver assembly, wherein the first driver assembly includes:
      (A) a laterally-opposed pair of distal drivers that receive respective staples of the plurality of staples,
      (B) a proximal driver that receives a respective staple of the plurality of staples, and
      (C) a cam surface,
   wherein the staple actuator is configured to engage the cam surface of the first driver assembly during distal translation of the staple actuator to drive the respective staples into contact with the anvil of the first jaw,
   wherein the staple actuator and the cam surface are configured such that, when the respective staples contact the anvil of the first jaw, the engagement between the staple actuator and the cam surface of the first driver assembly is centered at a location along the cam surface distal of a centroid of the first driver assembly,
   wherein the stapling assembly further includes:
(a) an elongate slot extending longitudinally for receiving a portion of the staple actuator; and
(b) at least one stapling assembly support member extending laterally inwardly from one side of the elongate slot toward an opposing side of the elongate slot,
wherein the at least one stapling assembly support member is configured to be deflected laterally outwardly by the portion of the staple actuator during distal translation of the staple actuator.

12. A surgical stapling instrument comprising:
(a) a shaft extending along a longitudinal axis to a distal end;
(b) an end effector operatively coupled with the shaft, wherein the end effector includes:
   (i) a first jaw having an anvil, and
   (ii) a second jaw, wherein the first and second jaws are operable to clamp tissue therebetween; and
(c) a stapling assembly supported by the second jaw of the end effector, wherein the stapling assembly includes:
   (i) a plurality of staples,
   (ii) a staple actuator translatable distally through the stapling assembly along the longitudinal axis, and
   (iii) a first driver assembly, wherein the first driver assembly includes:
      (A) a laterally-opposed pair of distal drivers that receive respective staples of the plurality of staples,
      (B) a proximal driver that receives a respective staple of the plurality of staples, and
      (C) a cam surface,
   wherein the staple actuator is configured to engage the cam surface of the first driver assembly during distal translation of the staple actuator to drive the respective staples into contact with the anvil of the first jaw,
   wherein the staple actuator and the cam surface are configured such that, when the respective staples contact the anvil of the first jaw, the engagement between the staple actuator and the cam surface of the first driver assembly is centered at a location along the cam surface distal of a centroid of the first driver assembly,
   wherein the stapling assembly further includes at least one driver retention member extending laterally inwardly to engage a portion of the first driver assembly, wherein the at least one driver retention member is configured to be deflected laterally outwardly by the portion of the first driver assembly during distal translation of the staple actuator.

13. The surgical stapling instrument of claim 1, wherein the stapling assembly further includes a cartridge comprising:
(a) a cartridge body; and
(b) a cartridge tray, wherein the staple actuator is captured between the cartridge body and the cartridge tray, wherein the cartridge tray includes at least one cartridge support member extending upwardly to engage a portion of the cartridge body, wherein the at least one cartridge support member is configured to be deflected downwardly by a portion of the staple actuator during distal translation of the staple actuator.

14. The surgical stapling instrument of claim 1, wherein the staple actuator includes:
(a) a base platform;
(b) a plurality of rails protruding upwardly from the base platform; and
(c) a central nose protruding upwardly and distally from the base platform.

15. A stapling assembly for a surgical stapling instrument, comprising:
(a) a plurality of staples;
(b) a staple actuator translatable distally through the stapling assembly along a longitudinal axis; and
(c) a driver assembly, wherein the driver assembly includes:
   (i) a laterally-opposed pair of distal drivers that receive respective staples of the plurality of staples,
   (ii) a proximal driver that receives a respective staple of the plurality of staples, wherein the proximal driver is positioned laterally between the pair of distal drivers, wherein at least a portion of the proximal driver is proximal of each of the pair of distal drivers, wherein the proximal driver is oriented substantially parallel relative to at least one of the pair of distal drivers, and
   (iii) a cam surface,
   wherein the staple actuator is configured to engage the cam surface of the driver assembly during distal translation of the staple actuator to drive the respective staples upwardly,
   wherein the staple actuator and the cam surface are configured such that, when the respective staples are driven between 0.05 inch and 0.065 inch upwardly from a starting position, the engagement between the staple actuator and the cam surface of the first driver assembly is centered at a location along the cam surface distal of a centroid of the first driver assembly.

16. The stapling assembly of claim 15, wherein the cam surface extends between a proximal cam surface end and a distal cam surface end, wherein the cam surface is inclined downwardly toward the distal cam surface end, wherein the distal cam surface end is substantially distal of the centroid.

17. The stapling assembly of claim 16, wherein the cam surface includes a midpoint between the proximal and distal cam surface ends, wherein the midpoint is substantially distal of the centroid.

18. The stapling assembly of claim 17, wherein the driver assembly further includes at least one rigger extending between the proximal driver and at least one of the distal drivers, wherein the cam surface is presented by the at least one rigger.

19. A method of operating an apparatus comprising (i) an end effector having an anvil and a jaw, and (ii) a stapling assembly supported by the jaw and having a staple actuator and a driver assembly having (A) a laterally-opposed pair of distal drivers that receive respective staples, (B) a proximal driver that receives a respective staple wherein the proximal driver is positioned laterally between the pair of distal drivers, wherein at least a portion of the proximal driver is proximal of each of the pair of distal drivers, wherein the proximal driver is oriented substantially parallel relative to at least one of the pair of distal drivers, and (C) a cam surface, the method comprising:

(a) translating the staple actuator distally through the stapling assembly along a longitudinal axis;
(b) engaging the staple actuator with the cam surface of the driver assembly to drive the respective staples into contact with the anvil;
(c) applying downward forces to distal ends of the distal drivers via the contact between the anvil and the respective staples; and
(d) simultaneously with the act of applying downward forces, applying an upward, distal force to the cam surface of the driver assembly via the staple actuator at a location along the cam surface distal of a centroid of the driver assembly, wherein the location is positioned below the centroid and spaced apart therefrom by a vertical distance, wherein the cam surface is oriented at an angle relative to a horizontal reference plane, wherein the vertical distance and the angle have a ratio of between approximately 0.025:25 and approximately 0.1:15.

20. The stapling assembly of claim 15, wherein the proximal driver is oriented substantially parallel relative to the longitudinal axis.

* * * * *